US008987531B2

(12) United States Patent
Grubbs et al.

(10) Patent No.: US 8,987,531 B2
(45) Date of Patent: Mar. 24, 2015

(54) SYNTHESES OF Z-OLEFIN-CONTAINING LEPIDOPTERAN INSECT PHEROMONES

(71) Applicant: California Institute of Technology, Pasadena, CA (US)

(72) Inventors: Robert H. Grubbs, South Pasadena, CA (US); Myles B. Herbert, Pasadena, CA (US); Zachary K. Wickens, Pasadena, CA (US); Vanessa M. Marx, Pasadena, CA (US); Benjamin K. Keitz, Pasadena, CA (US); Koji Endo, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 17 days.

(21) Appl. No.: 13/785,101

(22) Filed: Mar. 5, 2013

(65) Prior Publication Data
US 2013/0231499 A1    Sep. 5, 2013

Related U.S. Application Data

(60) Provisional application No. 61/606,847, filed on Mar. 5, 2012.

(51) Int. Cl.
| | |
|---|---|
| C07C 27/00 | (2006.01) |
| C07C 45/00 | (2006.01) |
| C07C 67/02 | (2006.01) |
| C07C 29/00 | (2006.01) |
| C07C 67/28 | (2006.01) |
| C07C 45/30 | (2006.01) |
| C07C 67/08 | (2006.01) |
| C07C 29/32 | (2006.01) |
| C07C 67/293 | (2006.01) |
| C07C 67/343 | (2006.01) |

(52) U.S. Cl.
CPC .............. C07C 29/00 (2013.01); C07C 67/28 (2013.01); C07C 45/30 (2013.01); C07C 67/08 (2013.01); C07C 29/32 (2013.01); C07C 67/293 (2013.01); C07C 67/343 (2013.01)
USPC ............ 568/904; 568/485; 568/404; 560/261

(58) Field of Classification Search
CPC ........ C07C 29/00; C07C 67/28; C07C 45/30; C07C 67/08; C07C 29/32; C07C 67/293; C07C 67/343
USPC ........................... 568/404, 485, 904; 560/261
See application file for complete search history.

(56) References Cited

U.S. PATENT DOCUMENTS

| | | | |
|---|---|---|---|
| 6,215,019 B1 * | 4/2001 | Pederson et al. ............ 560/234 |
| 6,696,597 B2 | 2/2004 | Pederson et al. | |
| 2002/0022741 A1 | 2/2002 | Pederson et al. | |
| 2005/0261451 A1 | 11/2005 | Ung et al. | |

2010/0144987 A1    6/2010   Vougioukaiakis et al.

FOREIGN PATENT DOCUMENTS

WO    WO2012032131    *  3/2012  ............... B01J 31/16
WO    WO 2012/097379        7/2012

OTHER PUBLICATIONS

Keitz et al., "Improved Ruthenium Catalysts for Z-selective Olefin Metathesis," J. Am. Chem. Soc., 134, 693-699, 2012 (published Nov. 19, 2011).*
Grubbs et al., "Z-Selective Homodimerization of Terminal Olefins with a Ruthenium Metathesis Catalyst," J. Am. Chem. Soc., 133, 9686-9688, 2011.*
Booij et al., "New Sex Attractants for 35 Tortricin and 4 Other Lepidopterous Species, Found by Systematic Field Screening in the Netherlands," Journal of Chemical Ecology, 10(1), 135-144, 1984.*
Urbina-Blanco et al., "Backbone tuning in indenylidene-ruthenium complexes bearing an unsaturated N-heterocyclic carbene," Beilstein Journal of Organic Chemistry, 6, 1120-1126, 2010.*
Chobanyan, "Preparative Synthesis of (Z)-5-decenyl Acetate," Russian Journal of Applied Chemistry, 77(12), 2036-2037, 2004.*
Clavier et al., "Percent buried volume for phosphine and N-heterocyclic carbine ligands: steric properties in organometallic chemistry", Chem. Comm., 2010, 46, 841-861.
Endo et al., "Chelated Ruthenium Catalysts for Z-Selective Olefin Methesis", Journal of the American Chemical Society, 2011, 133, 8525-8527.
Herbert et al., "Concise Sytheses of Insect Pheromones Using Z-Selective Cross Metathesis", Angewandte Chemie International Edition, 2013, 52, 310-314.
Herbert et al., "Decomposition Pathways of Z-Selective Ruthenium Metathesis Catalysts", Journal of the American Chemical Society, 2012, 134, 7861-7866.
Keitz et al., "Cis-Selective Ring-Opening Metathesis Polymerization with Ruthenium Catalysts", Journal of the American Chemical Society, 2012, 134, 2040-2043.
Keitz et al., "Improved Ruthenium Catalysts for Z-Selective Olefin Metatesis", Journal of the American Chemical Society, 2012, 134, 693-699.
Keitz et al., "Z-Selective Homodimerization of Terminal Olefins with a Ruthenium Metathesis Catalyst", Journal of the American Chemical Society, 2011, 133, 9686-9688.
Liu et al., "Z-Selective in Olefin Metatheiss with Chelated Ru Catalysts: Computational Studies of Mechanism and Selectivity", Journal of the American Chemical Society, 2012, 134, 1464-1467.
Marx et al., "Stereoselective Access to Z and E Macrocycles by Ruthenium-Catalyzed Z-Selective Ring Closing Metathesis and Ethenolysis", Journal of the American Chemical Society, 2013, 135, 94-97.
Pederson et al., "Applications of Olefin Cross Metathesis to Commercial Products", Adv. Synth. Catal., Aug. 2002, 344, 728-735.
Rosebrugh et al., "Highly Active Ruthenium Metathesis Catalysts Exhibiting Unprecedented Activity and Z-Selectivity", Journal of the American Chemical Society, 2013, 135, 1276-1279.

* cited by examiner

Primary Examiner — Paul A Zucker
Assistant Examiner — Mark Luderer
(74) Attorney, Agent, or Firm — Baker & Hostetler LLP

(57) ABSTRACT

The present invention is directed to methods of synthesizing insect pheromones, particularly lepidopteran insect pheromones, their precursors and derivatives from inexpensive, readily available starting materials using olefin metathesis catalysis.

30 Claims, 3 Drawing Sheets

SYNTHESES OF Z-OLEFIN-CONTAINING LEPIDOPTERAN INSECT PHEROMONES

CROSS REFERENCE TO RELATED APPLICATIONS

This application claims priority to U.S. Application No. 61/606,847, filed Mar. 5, 2012, which is incorporated by reference herein in its entirety.

GOVERNMENT RIGHTS

The subject matter disclosed herein was made with government support under award/contract/grant number GM031332 awarded by the National Institutes of Health and CHE1048404 awarded by the National Science Foundation. The Government has certain rights in the herein disclosed subject matter.

TECHNICAL FIELD

The present invention(s) relates to synthetic insect pheromones, their precursors and derivatives, and methods of making the same.

BACKGROUND

The use of insect pheromones to control specifically targeted pest populations has gained increasing popularity as a viable, safe, and environmentally-friendly alternative to broad spectrum insecticides. To date, the environmental protection agency (EPA) has approved approximately twenty female sex pheromones of the lepidopteran order of insects as active ingredients for pest control. A major factor hindering more widespread use of pheromones for pest control is the production cost of synthetic pheromones.

The lepidopteran order of insects includes large families of butterflies and moths whose larvae can devastate critical and valuable crops. Two pheromone-based pest control methods are used primarily, mass trapping and mating disruption. With the former method, female sex pheromones are placed in a trap that attracts and kills male insects. Mating disruption involves dispersing pheromones over a large area, effectively overloading the sensory organs of male insects and preventing them from being able to locate females that are releasing a much smaller amount of the same pheromones. This synergistic effect prevents mating and has been shown to reduce specific insect populations dramatically. Pheromones also play an essential role in integrated pest management (IPM), which involves monitoring insect populations and using appropriate, cost-effective pest control methods. The amount of insects captured in pheromone traps is correlated to the pest's population, which allows for a more targeted approach, reducing wasteful practices.

Pheromones of the lepidopteran order of insects are traditionally defined as straight chained hydrocarbon acetates, alcohols, or aldehydes containing 10 to 18 carbons and 1 to 3 double bonds with various olefin geometries. The presence of functional groups and alkenes makes ruthenium-based olefin metathesis an attractive methodology for the synthesis of these species. The synthesis of trans-olefin containing mono- and di-unsaturated pheromones utilizing olefin metathesis has been accomplished. The efficient synthesis of cis-containing pheromones has remained a challenge. Current synthesis of such species involves inefficient and costly processes, including the use of acetylene and poisoned hydrogenation catalysts.

SUMMARY

The present invention provides methods by which commercially useful cis-olefins may be prepared in high yield at ambient conditions in fewer steps, in some cases with the use of starting materials derived from commodity materials like α-olefins and seed oils. More generally, the methodologies described herein provide a valuable tool in providing this cis-olefin functionality for high value agrichemicals and pharmaceuticals. The ruthenium metathesis catalysts described herein can be modified to control efficiency and selectivity. Consequently, other ruthenium based catalysts that demonstrate Z-selectivity in homodimerizations will also be efficient catalysts for the synthesis of Z-pheromones and other structures containing cis-olefins.

Certain embodiments of the present invention include methods of synthesizing Z-olefin metathesis products. Individual, specific embodiments provide that this Z-olefin metathesis product is an insect pheromone, a lepidopteran insect pheromone, and separately cyclic and acyclic insect or lepidopteran insect pheromones, each containing a Z-olefin metathesis product, each method comprising:

(a) cross-metathesizing (i) a terminal olefin and an internal olefin or (ii) two terminal olefins in the presence of a hindered ruthenium metathesis catalyst to form the insect pheromone Z-olefin metathesis product and a side product;

the hindered metathesis catalyst comprising a C—H activated olefin metathesis catalyst compound having a structure of Formula I,

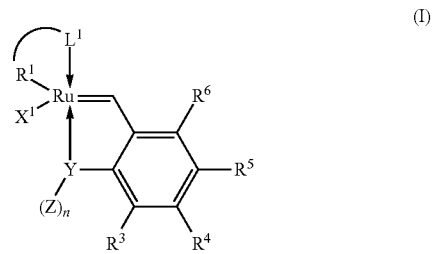

wherein
$X^1$ is an anionic ligand;
$L^1$ is a carbene ligand having the structure of Formula (II):

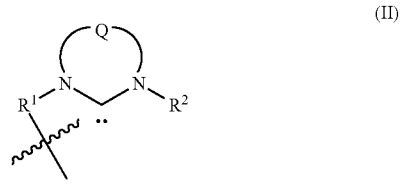

wherein,
Q is selected from hydrocarbylene, substituted hydrocarbylene, heteroatom-containing hydrocarbylene, or substituted heteroatom-containing hydrocarbylene, wherein two or more substituents on adjacent atoms within Q may also be linked to form an additional cyclic structure;
$R^1$ is an optionally substituted hydrocarbylene or an optionally substituted heteroatom-containing hydrocarbylene, where $R^1$ links $L^1$ and M and, together with $L^1$ and M, form one or more cyclic groups, and wherein M, $L^1$ and $R^1$ form an M-$R^1$-$L^1$ chelating ligand ring structure having a ring size of 5, 6, or 7 atoms;

R² is an optionally substituted hydrocarbyl or an optionally substituted heteroatom-containing hydrocarbyl;

Y is N, O, S, or P (or other two electron donors);

R³, R⁴, R⁵, and R⁶ are each, independently, hydrogen, halogen, alkyl, alkenyl, alkynyl, aryl, heteroalkyl, heteroatom containing alkenyl, heteroalkenyl, heteroaryl, alkoxy, alkenyloxy, aryloxy, alkoxycarbonyl, carbonyl, alkylamino, alkylthio, aminosulfonyl, monoalkylaminosulfonyl, dialkylaminosulfonyl, alkylsulfonyl, nitrile, nitro, alkylsulfinyl, trihaloalkyl, perfluoroalkyl, carboxylic acid, ketone, aldehyde, nitrate, cyano, isocyanate, hydroxyl, ester, ether, amine, imine, amide, halogen-substituted amide, trifluoroamide, sulfide, disulfide, sulfonate, carbamate, silane, siloxane, phosphine, phosphate, or borate, wherein any combination of R⁵, R⁶, R⁷, and R⁸ can be linked to form one or more cyclic groups;

n is 1 or 2, such that n is 1 for the divalent heteroatoms O or S, and n is 2 for the trivalent heteroatoms N or P; and Z is selected from hydrogen, alkyl, aryl, functionalized alkyl, or functionalized aryl wherein the functional group(s) may independently comprise one or more or the following: alkoxy, aryloxy, halogen, carboxylic acid, ketone, aldehyde, nitrate, cyano, isocyanate, hydroxyl, ester, ether, amine, imine, amide, trifluoroamide, sulfide, disulfide, carbamate, silane, siloxane, phosphine, phosphate, or borate; methyl, isopropyl, sec-butyl, t-butyl, neopentyl, benzyl, phenyl and trimethylsilyl; and wherein any combination or combinations of X¹, R¹, R², L¹, Y, Z, R³, R⁴, R⁵, and R⁶ are optionally linked to a support.

Additional embodiments provide for a range of catalyst, including those where where Q is an optionally substituted ethylene (—CH₂CH₂—), R¹ is an optionally substituted adamantylene, R² is 2,4,6-trimethyl phenyl (mesityl), methylisopropylphenyl (MIPP), or di-isopropylphenyl (DIPP); X¹ is nitrate or pivalate, R³, R⁴, R⁵, and R⁶ are each hydrogen; Y is O; and (Z)ₙ is isopropyl.

Additional embodiments provide for a ranger of substrate and product options, as well as suitable processing conditions. Suitable products include those of the formula: 3, 5-10, 12-13, 15-17, 19-22, or 24:

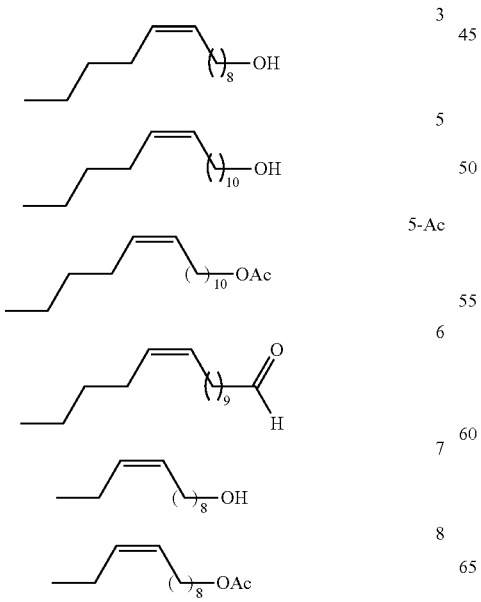

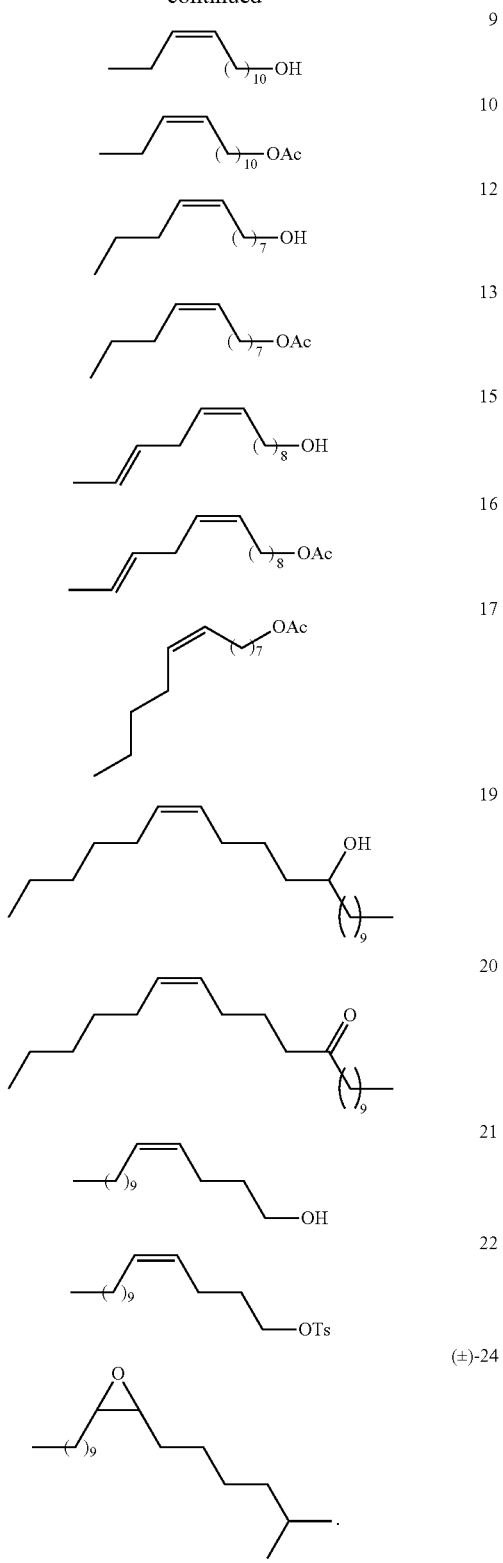

Certain specific embodiments provide various methods for providing insect pheromones, the methods comprising cross-metathesizing:

(a) oleyl alcohol and 1-hexene in the presence of a hindered ruthenium metathesis catalyst to form (Z)-tetradec-9-en-1-ol (3) and 1-decene;

(b) 11-eicosenol and 1-hexene in the presence of a hindered ruthenium metathesis catalyst to form (Z)-hexadec-11-en-1-ol (5) and 1-decene; the (Z)-hexadec-11-en-1-ol (5) is optionally separated from the 1-decene, and further oxidized to form (Z)-hexadec-11-enal (6).

(c) oleyl alcohol and 1-butene in the presence of a hindered ruthenium metathesis catalyst to form (Z)-dodec-9-en-1-ol (7) and 1-decene; the (Z)-dodec-9-en-1-ol (7) is optionally separated from the 1-decene, and acetylated to form (Z)-dodec-9-en-1-yl acetate (8);

(d) 11-eicosenol and 1-butene in the presence of a hindered ruthenium metathesis catalyst to form (Z)-tetradec-11-en-1-ol (9) and 1-decene; the (Z)-tetradec-11-en-1-ol (9) is optionally separated from the 1-decene, and acetylated to form (Z)-tetradec-11-en-1-yl acetate (10);

(e) 8-nonenol and 1-pentene in the presence of a hindered ruthenium metathesis catalyst to form (Z)-dodec-8-en-1-ol (12) and ethylene; the (Z)-dodec-8-en-1-ol (12) is optionally separated from the ethylene and acetylated to form (Z)-dodec-8-en-1-yl acetate (13);

(f) 8-nonenyl acetate and 1-pentene in the presence of a hindered ruthenium metathesis catalyst to form (Z)-dodec-8-en-1-yl acetate (13) and ethylene;

(g) oleyl alcohol and 1,4-trans-hexadiene in the presence of a hindered ruthenium metathesis catalyst to form (9Z,12E)-tetradeca-9,12-dien-ol (15) and 1-decene; the (9Z,12E)-tetradeca-9,12-dien-ol (15) is optionally separated from the 1-decene, and acetylated to form (9Z,12E)-tetradeca-9,12-dien-yl acetate (16);

(h) (Z)-hexadec-1-6-ol and 1-heptene to form (Z)-henicos-6-en-11-ol (19) and ethylene; the (Z)-henicos-6-en-11-ol (19) is optionally separated from the ethylene, and oxidized to form (Z)-henicos-6-en-11-one (20);

(i) 4-pentan-1-ol and 1-dodecene in the presence of a hindered ruthenium metathesis catalyst to form (Z)-pentadec-4-en-1-ol (21) and ethylene.

BRIEF DESCRIPTION OF THE DRAWINGS

The present application is further understood when read in conjunction with the appended drawings. For the purpose of illustrating the subject matter, there are shown in the drawings exemplary embodiments of the subject matter; however, the presently disclosed subject matter is not limited to the specific methods, devices, and systems disclosed. In addition, the drawings are not necessarily drawn to scale. In the drawings.

DETAILED DESCRIPTION OF ILLUSTRATIVE EMBODIMENTS

General Remarks

Figure 1:
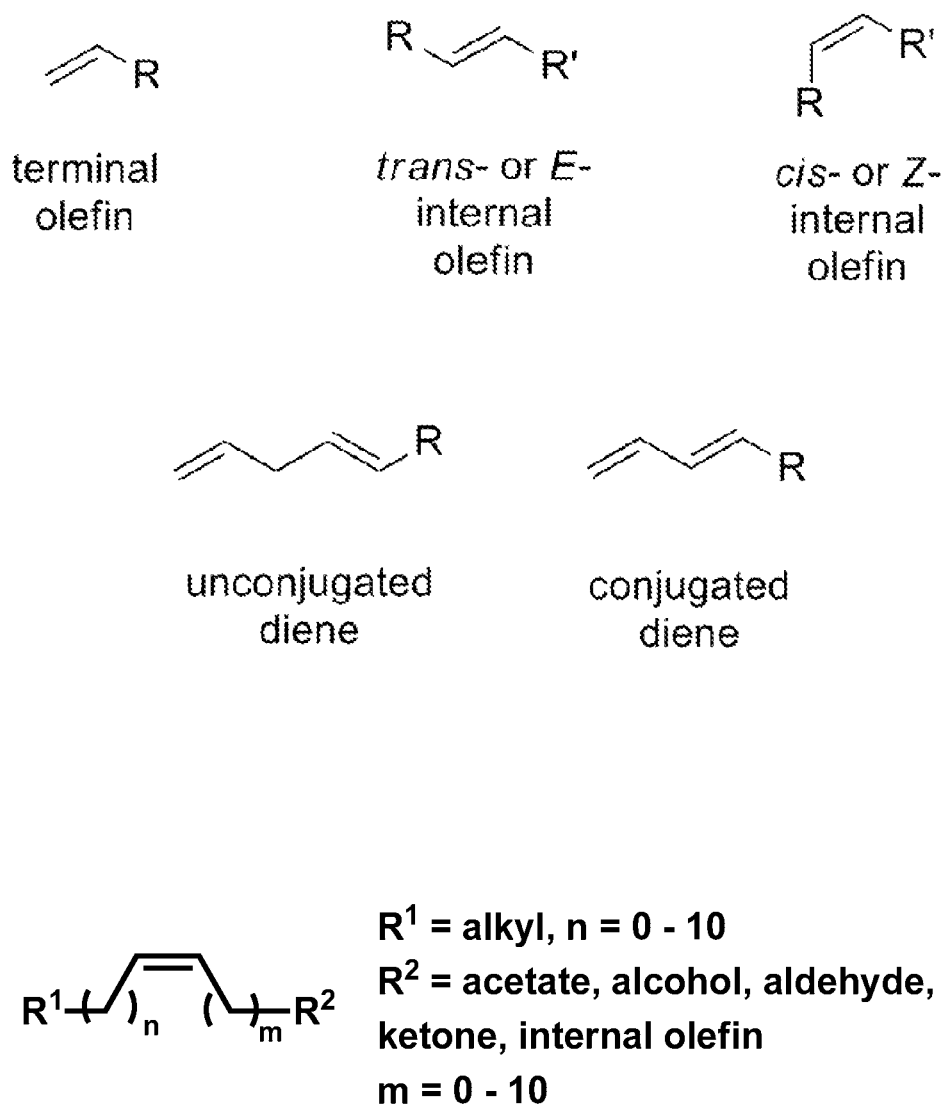
FIG. 1 illustrates the nomenclatures used in the structures described herein, including the general structures of some cis-pheromones of interest.

The present invention may be understood more readily by reference to the following description taken in connection with the accompanying Figures and Examples, all of which form a part of this disclosure. It is to be understood that this invention is not limited to the specific products, methods, conditions or parameters described and/or shown herein, and that the terminology used herein is for the purpose of describing particular embodiments by way of example only and is not intended to be limiting of any claimed invention. Similarly, unless specifically otherwise stated, any description as to a possible mechanism or mode of action or reason for improvement is meant to be illustrative only, and the invention herein is not to be constrained by the correctness or incorrectness of any such suggested mechanism or mode of action or reason for improvement. Throughout this text, it is recognized that the descriptions refer both to the methods of preparing the desired products, as well as the use of the products so prepared, and vice versa.

In the present disclosure the singular forms "a," "an," and "the" include the plural reference, and reference to a particular numerical value includes at least that particular value, unless the context clearly indicates otherwise. Thus, for example, a reference to "a material" is a reference to at least one of such materials and equivalents thereof known to those skilled in the art, and so forth.

When a value is expressed as an approximation by use of the descriptor "about," it will be understood that the particular value forms another embodiment. In general, use of the term "about" indicates approximations that can vary depending on the desired properties sought to be obtained by the disclosed subject matter and is to be interpreted in the specific context in which it is used, based on its function. The person skilled in the art will be able to interpret this as a matter of routine. In some cases, the number of significant figures used for a particular value may be one non-limiting method of determining the extent of the word "about." In other cases, the gradations used in a series of values may be used to determine the intended range available to the term "about" for each value. Where present, all ranges are inclusive and combinable. That is, references to values stated in ranges include every value within that range.

When a list is presented, unless stated otherwise, it is to be understood that each individual element of that list and every combination of that list is to be interpreted as a separate embodiment. For example, a list of embodiments presented as "A, B, or C" is to be interpreted as including the embodiments, "A," "B," "C," "A or B," "A or C," "B or C," or "A, B, or C."

It is to be appreciated that certain features of the invention which are, for clarity, described herein in the context of separate embodiments, may also be provided in combination in a single embodiment. That is, unless obviously incompatible or specifically excluded, each individual embodiment is deemed to be combinable with any other embodiment(s) and such a combination is considered to be another embodiment. Conversely, various features of the invention that are, for brevity, described in the context of a single embodiment, may also be provided separately or in any sub-combination. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Finally, while an embodiment may be described as part of a series of steps or part of a more general structure, each said step or part may also be considered an independent embodiment in itself.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are described herein.

In this specification and in the claims that follow, reference will be made to a number of terms, which shall be defined to have the following meanings:

The terms "Z-olefin" and "cis-olefin" both refer to a 1,2 disubstituted olefin structure where the substituents are positioned on the same side of the olefin, as shown in FIG. 1. The terms "E-olefin" and "trans-olefin" both refer to a 1,2 disubstituted olefin structure where the substituents are positioned on the opposite side of and across the olefin double bond, also as shown in FIG. 1.

The term "alkyl" as used herein refers to a linear, branched, or cyclic saturated hydrocarbon group typically although not necessarily containing 1 to about 24 carbon atoms, preferably 1 to about 12 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl and the like. Generally, although again not necessarily, alkyl groups herein contain 1 to about 12 carbon atoms. The term "lower alkyl" intends an alkyl group of 1 to 6 carbon atoms, and the specific term "cycloalkyl" intends a cyclic alkyl group, typically having 4 to 8, preferably 5 to 7, carbon atoms. The term "substituted alkyl" refers to alkyl groups substituted with one or more substituent groups, and the terms "heteroatom-containing alkyl" and "heteroalkyl" refer to alkyl groups in which at least one carbon atom is replaced with a heteroatom. If not otherwise indicated, the terms "alkyl" and "lower alkyl" include linear, branched, cyclic, unsubstituted, substituted, and/or heteroatom-containing alkyl and lower alkyl groups, respectively.

The term "alkylene" as used herein refers to a difunctional linear, branched, or cyclic alkyl group, where "alkyl" is as defined above.

The term "alkenyl" as used herein refers to a linear, branched, or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, and the like. Preferred alkenyl groups herein contain 2 to about 12 carbon atoms. The term "lower alkenyl" intends an alkenyl group of 2 to 6 carbon atoms, and the specific term "cycloalkenyl" intends a cyclic alkenyl group, preferably having 5 to 8 carbon atoms. The term "substituted alkenyl" refers to alkenyl groups substituted with one or more substituent groups, and the terms "heteroatom-containing alkenyl" and "heteroalkenyl" refer to alkenyl groups in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl groups, respectively.

The term "alkenylene" as used herein refers to a difunctional linear, branched, or cyclic alkenyl group, where "alkenyl" is as defined above.

The term "alkynyl" as used herein refers to a linear or branched hydrocarbon group of 2 to about 24 carbon atoms containing at least one triple bond, such as ethynyl, n-propynyl, and the like. Preferred alkynyl groups herein contain 2 to about 12 carbon atoms. The term "lower alkynyl" intends an alkynyl group of 2 to 6 carbon atoms. The term "substituted alkynyl" refers to an alkynyl group substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include a linear, branched, unsubstituted, substituted, and/or heteroatom-containing alkynyl and lower alkynyl group, respectively.

The term "alkoxy" as used herein intends an alkyl group bound through a single, terminal ether linkage; that is, an "alkoxy" group may be represented as -O-alkyl where alkyl is as defined above. A "lower alkoxy" group intends an alkoxy group containing 1 to 6 carbon atoms. Analogously, "alkenyloxy" and "lower alkenyloxy" respectively refer to an alkenyl and lower alkenyl group bound through a single, terminal ether linkage, and "alkynyloxy" and "lower alkynyloxy" respectively refer to an alkynyl and lower alkynyl group bound through a single, terminal ether linkage.

The term "aryl" as used herein, and unless otherwise specified, refers to an aromatic substituent containing a single aromatic ring or multiple aromatic rings that are fused together, directly linked, or indirectly linked (such that the different aromatic rings are bound to a common group such as a methylene or ethylene moiety). Preferred aryl groups contain 5 to 24 carbon atoms, and particularly preferred aryl groups contain 5 to 14 carbon atoms. Exemplary aryl groups contain one aromatic ring or two fused or linked aromatic rings, e.g., phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to aryl substituents in which at least one carbon atom is replaced with a heteroatom, as will be described in further detail infra.

The term "aryloxy" as used herein refers to an aryl group bound through a single, terminal ether linkage, wherein "aryl" is as defined above. An "aryloxy" group may be represented as —O-aryl where aryl is as defined above. Preferred aryloxy groups contain 5 to 24 carbon atoms, and particularly preferred aryloxy groups contain 5 to 14 carbon atoms. Examples of aryloxy groups include, without limitation, phenoxy, o-halo-phenoxy, m-halo-phenoxy, p-halo-phenoxy, o-methoxy-phenoxy, m-methoxy-phenoxy, p-methoxy-phenoxy, 2,4-dimethoxy-phenoxy, 3,4,5-trimethoxy-phenoxy, and the like.

The term "alkaryl" refers to an aryl group with an alkyl substituent, and the term "aralkyl" refers to an alkyl group with an aryl substituent, wherein "aryl" and "alkyl" are as defined above. Preferred alkaryl and aralkyl groups contain 6 to 24 carbon atoms, and particularly preferred alkaryl and aralkyl groups contain 6 to 16 carbon atoms. Alkaryl groups include, for example, p-methylphenyl, 2,4-dimethylphenyl, p-cyclohexylphenyl, 2,7-dimethylnaphthyl, 7-cyclooctylnaphthyl, 3-ethyl-cyclopenta-1,4-diene, and the like. Examples of aralkyl groups include, without limitation, benzyl, 2-phenyl-ethyl, 3-phenyl-propyl, 4-phenyl-butyl, 5-phenyl-pentyl, 4-phenylcyclohexyl, 4-benzylcyclohexyl, 4-phenylcyclohexylmethyl, 4-benzylcyclohexylmethyl, and the like. The terms "alkaryloxy" and "aralkyloxy" refer to substituents of the formula —OR wherein R is alkaryl or aralkyl, respectively, as just defined.

The term "acyl" refers to substituents having the formula —(CO)-alkyl, —(CO)-aryl, or —(CO)-aralkyl, and the term "acyloxy" refers to substituents having the formula —O(CO)-alkyl, —O(CO)-aryl, or —O(CO)-aralkyl, wherein "alkyl," "aryl, and "aralkyl" are as defined above.

The terms "cyclic" and "ring" refer to alicyclic or aromatic groups that may or may not be substituted and/or heteroatom-containing, and that may be monocyclic, bicyclic, or polycyclic. The term "alicyclic" is used in the conventional sense to refer to an aliphatic cyclic moiety, as opposed to an aromatic cyclic moiety, and may be monocyclic, bicyclic, or polycyclic. The term "acyclic" refers to a structure in which the double bond is not contained within a ring structure.

The terms "halo" and "halogen" are used in the conventional sense to refer to a chloro, bromo, fluoro, or iodo substituent.

"Hydrocarbyl" refers to univalent hydrocarbyl radicals containing 1 to about 30 carbon atoms, preferably 1 to about 24 carbon atoms, most preferably 1 to about 12 carbon atoms, including linear, branched, cyclic, saturated, and unsaturated species, such as alkyl groups, alkenyl groups, aryl groups, and the like. The term "lower hydrocarbyl" intends a hydrocarbyl group of 1 to 6 carbon atoms, preferably 1 to 4 carbon atoms, and the term "hydrocarbylene" intends a divalent hydrocarbyl moiety containing 1 to about 30 carbon atoms, preferably 1 to about 24 carbon atoms, most preferably 1 to about 12 carbon atoms, including linear, branched, cyclic, saturated and unsaturated species. The term "lower hydrocarbylene" intends a hydrocarbylene group of 1 to 6 carbon atoms. "Substituted hydrocarbyl" refers to hydrocarbyl substituted with one or more substituent groups, and the terms "heteroatom-containing hydrocarbyl" and "heterohydrocarbyl" refer to hydrocarbyl in which at least one carbon atom is replaced with a heteroatom. Similarly, "substituted hydrocarbylene" refers to hydrocarbylene substituted with one or more substituent groups, and the terms "heteroatom-containing hydrocarbylene" and "heterohydrocarbylene" refer to hydrocarbylene in which at least one carbon atom is replaced with a heteroatom. Unless otherwise indicated, the term "hydrocarbyl" and "hydrocarbylene" are to be interpreted as including substituted and/or heteroatom-containing hydrocarbyl and hydrocarbylene moieties, respectively.

The term "heteroatom-containing" as in a "heteroatom-containing hydrocarbyl group" refers to a hydrocarbon molecule or a hydrocarbyl molecular fragment in which one or more carbon atoms is replaced with an atom other than carbon, e.g., nitrogen, oxygen, sulfur, phosphorus or silicon, typically nitrogen, oxygen or sulfur. Similarly, the term "heteroalkyl" refers to an alkyl substituent that is heteroatom-containing, the term "heterocyclic" refers to a cyclic substituent that is heteroatom-containing, the terms "heteroaryl" and heteroaromatic" respectively refer to "aryl" and "aromatic" substituents that are heteroatom-containing, and the like. It should be noted that a "heterocyclic" group or compound may or may not be aromatic, and further that "heterocycles" may be monocyclic, bicyclic, or polycyclic as described above with respect to the term "aryl." Examples of heteroalkyl groups include alkoxyaryl, alkylsulfanyl-substituted alkyl, N-alkylated amino alkyl, and the like. Examples of heteroaryl substituents include pyrrolyl, pyrrolidinyl, pyridinyl, quinolinyl, indolyl, pyrimidinyl, imidazolyl, 1,2,4-triazolyl, tetrazolyl, etc., and examples of heteroatom-containing alicyclic groups are pyrrolidino, morpholino, piperazino, piperidino, etc.

By "substituted" as in "substituted hydrocarbyl," "substituted alkyl," "substituted aryl," and the like, as alluded to in some of the aforementioned definitions, is meant that in the hydrocarbyl, alkyl, aryl, or other moiety, at least one hydrogen atom bound to a carbon (or other) atom is replaced with one or more non-hydrogen substituents. Examples of such substituents include, without limitation: functional groups referred to herein as "Fn," such as halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{24}$ aryloxy, $C_6$-$C_{24}$ aralkyloxy, $C_6$-$C_{24}$ alkaryloxy, acyl (including $C_1$-$C_{24}$ alkylcarbonyl (—CO-alkyl) and $C_6$-$C_{24}$ arylcarbonyl (—CO-aryl)), acyloxy (—O-acyl, including $C_2$-$C_{24}$ alkylcarbonyloxy (—O—CO-alkyl) and $C_6$-$C_{24}$ arylcarbonyloxy (—O—CO-aryl)), $C_2$-$C_{24}$ alkoxycarbonyl ((CO)—O-alkyl), $C_6$-$C_{24}$ aryloxycarbonyl (—(CO)—O-aryl), halocarbonyl (—CO)—X where X is halo), $C_2$-$C_{24}$ alkylcarbonato (—O—(CO)—O-alkyl), $C_6$-$C_{24}$ arylcarbonato (—O—(CO)—O-aryl), carboxy (—COOH), carboxylato (—COO—), carbamoyl (—(CO)—NH$_2$), mono-($C_1$-$C_{24}$ alkyl)-substituted carbamoyl (—(CO)NH($C_1$-$C_{24}$ alkyl)), di-($C_1$-$C_{24}$ alkyl)-substituted carbamoyl (—(CO)—N($C_1$-$C_{24}$ alkyl)$_2$), mono-($C_1$-$C_{24}$ haloalkyl)-substituted carbamoyl (—(CO)—NH($C_1$-$C_{24}$ alkyl)), di-($C_1$-$C_{24}$ haloalkyl)-substituted carbamoyl (—(CO)—N($C_1$-$C_{24}$ alkyl)$_2$), mono-($C_5$-$C_{24}$ aryl)-substituted carbamoyl (—(CO)—NH-aryl), di-($C_5$-$C_{24}$ aryl)substituted carbamoyl (—(CO)—N($C_5$-$C_{24}$ aryl)$_2$), di-N—($C_1$-$C_{24}$ alkyl), N—($C_5$-$C_{24}$ aryl)-substituted carbamoyl, thiocarbamoyl (—(CS)—NH$_2$), mono-($C_1$-$C_{24}$ alkyl)-substituted thiocarbamoyl (—(CO)—NH($C_1$-$C_{24}$ alkyl)), di-($C_1$-$C_{24}$ alkyl)-substituted thiocarbamoyl (—(CO)—N($C_1$-$C_{24}$ alkyl)$_2$), mono-($C_5$-$C_{24}$ aryl)substituted thiocarbamoyl (—(CO)—NH-aryl), di-($C_5$-$C_{24}$ aryl)-substituted thiocarbamoyl (—(CO)—N($C_5$-$C_{24}$ aryl)$_2$), di-N—($C_1$-$C_{24}$ alkyl), N—($C_5$-$C_{24}$ aryl)-substituted thiocarbamoyl, carbamido (—NH—(CO)—NH$_2$), cyano(—C≡N), cyanato (—O—C≡N), thiocyanato (—S—C≡N), formyl (—(CO)—H), thioformyl (—(CS)—H), amino (—NH$_2$), mono-($C_1$-$C_{24}$ alkyl)-substituted amino, di-($C_1$-$C_{24}$ alkyl)-substituted amino, mono-($C_5$-$C_{24}$ aryl)substituted amino, di-($C_5$-$C_{24}$ aryl)-substituted amino, $C_1$-$C_{24}$ alkylamido (—NH—(CO)-alkyl), $C_6$-$C_{24}$ arylamido (—NH—(CO)-aryl), imino (—CR=NH where R=hydrogen, $C_1$-$C_{24}$ alkyl, C5-C24 aryl, $C_6$-$C_{24}$ alkaryl, $C_6$-$C_{24}$ aralkyl, etc.), $C_2$-$C_{20}$ alkylimino (—CR=N(alkyl), where R=hydrogen, $C_1$-$C_{24}$ alkyl, $C_5$-$C_{24}$ aryl, $C_6$-$C_{24}$ alkaryl, $C_6$-$C_{24}$ aralkyl, etc.), arylimino (—CR=N (aryl), where R=hydrogen, $C_1$-$C_{20}$ alkyl, $C_5$-$C_{24}$ aryl, $C_6$-$C_{24}$ alkaryl, $C_6$-$C_{24}$ aralkyl, etc.), nitro (—NO$_2$), nitroso (—NO), sulfo (—SO$_2$OH), sulfonate (SO$_2$O—), $C_1$-$C_{24}$ alkylsulfanyl (—S-alkyl; also termed "alkylthio"), $C_5$-$C_{24}$ arylsulfanyl (—S-aryl; also termed "arylthio"), $C_1$-$C_{24}$ alkylsulfinyl (—(SO)-alkyl), $C_5$-$C_{24}$ arylsulfinyl (—(SO)-aryl), $C_1$-$C_{24}$ alkylsulfonyl (—SO$_2$-alkyl), $C_1$-$C_{24}$ monoalkylaminosulfonyl-SO$_2$—N(H) alkyl), $C_1$-$C_{24}$ dialkylaminosulfonyl-SO$_2$—N(alkyl)$_2$, $C_5$-$C_{24}$ arylsulfonyl (—SO$_2$-aryl), boryl (—BH$_2$), borono (—B(OH)$_2$), boronato (—B(OR)$_2$ where R is alkyl or other hydrocarbyl), phosphono (—P(O)(OH)$_2$), phosphonato (—P(O)(O)$_2$), phosphinato (P(O)(O—)), phospho (—PO$_2$), and phosphine (—PH$_2$); and the hydrocarbyl moieties $C_1$-$C_{24}$ alkyl (preferably $C_1$-$C_{12}$ alkyl, more preferably $C_1$-$C_6$ alkyl), $C_2$-$C_{24}$ alkenyl (preferably $C_2$-$C_{12}$ alkenyl, more preferably $C_2$-$C_6$ alkenyl), $C_2$-$C_{24}$ alkynyl (preferably $C_2$-$C_{12}$ alkynyl, more preferably C2-C6 alkynyl), $C_5$-$C_{24}$ aryl (preferably $C_5$-$C_{24}$ aryl), $C_6$-$C_{24}$ alkaryl (preferably $C_6$-$C_{16}$ alkaryl), and $C_6$-$C_{24}$ aralkyl (preferably $C_6$-$C_{16}$ aralkyl).

By "functionalized" as in "functionalized hydrocarbyl," "functionalized alkyl," "functionalized olefin," "functionalized cyclic olefin," and the like, is meant that in the hydrocarbyl, alkyl, olefin, cyclic olefin, or other moiety, at least one hydrogen atom bound to a carbon (or other) atom is replaced with one or more functional groups such as those described herein and above. The term "functional group" is meant to include any functional species that is suitable for the uses described herein. In particular, as used herein, a functional group would necessarily possess the ability to react with or bond to corresponding functional groups on a substrate surface.

In addition, the aforementioned functional groups may, if a particular group permits, be further substituted with one or more additional functional groups or with one or more hydrocarbyl moieties such as those specifically enumerated above. Analogously, the above-mentioned hydrocarbyl moieties may be further substituted with one or more functional groups or additional hydrocarbyl moieties such as those specifically enumerated.

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

The present invention provides methods by which commercially useful cis-olefins may be prepared in high yield at ambient conditions. While synthesis of cis-olefins (Z-olefins) are thermodynamically less favored than trans-olefins (E-olefins), through use of the particular ruthenium metathesis catalysts defined herein, the products may be prepared in fewer steps than other synthetic schemes, with the use of starting materials derived from commodity materials like α-olefins and seed oils. More generally, the methodologies described herein provide for a valuable tool in providing this cis-olefin functionality for polymers, high value agrichemicals, flavors and fragrances, nutraceuticals, pharmaceuticals, and other fine chemicals. The ruthenium metathesis catalysts described herein can be modified to control efficiency and selectivity. Consequently, other ruthenium-based catalysts that demonstrate Z-selectivity in homodimerizations will also be efficient catalysts for the synthesis of Z-pheromones and other structures containing cis-olefins.

Certain embodiments of the present invention include methods of synthesizing a Z-olefin metathesis product. Individual, specific embodiments provide that this Z-olefin metathesis product is an insect pheromone, a lepidopteran insect pheromone, and separately cyclic and acyclic insect or lepidopteran insect pheromones, each containing a Z-olefin metathesis product, each method comprising:

(a) cross-metathesizing (i) a terminal olefin and an internal olefin or (ii) two terminal olefins in the presence of a hindered ruthenium metathesis catalyst to form the Z-olefin metathesis product and a side product;

the hindered metathesis catalyst comprising a C—H activated olefin metathesis catalyst compound having a structure of Formula I,

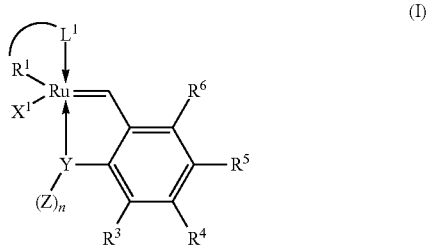

(I)

wherein $X^1$ is an anionic ligand;

$L^1$ is a carbene ligand having the structure of Formula (II):

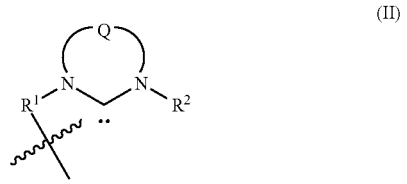

(II)

wherein,

Q is selected from hydrocarbylene, substituted hydrocarbylene, heteroatom-containing hydrocarbylene, or substituted heteroatom-containing hydrocarbylene, wherein two or more substituents on adjacent atoms within Q may also be linked to form an additional cyclic structure;

$R^1$ is an optionally substituted hydrocarbylene or an optionally substituted heteroatom-containing hydrocarbylene, where $R^1$ links $L^1$ and M and, together with $L^1$ and M, form one or more cyclic groups, and wherein M, $L^1$ and $R^1$ form an M-$R^1$-$L^1$ chelating ligand ring structure having a ring size of 5, 6, or 7 atoms;

$R^2$ is an optionally substituted hydrocarbyl or an optionally substituted heteroatom-containing hydrocarbyl'

Y is N, O, S, or P (or other two electron donor);

$R^3$, $R^4$, $R^5$, and $R^6$ are each, independently, hydrogen, halogen, alkyl, alkenyl, alkynyl, aryl, heteroalkyl, heteroatom containing alkenyl, heteroalkenyl, heteroaryl, alkoxy, alkenyloxy, aryloxy, alkoxycarbonyl, carbonyl, alkylamino, alkylthio, aminosulfonyl, monoalkylaminosulfonyl, dialkylaminosulfonyl, alkylsulfonyl, nitrile, nitro, alkylsulfinyl, trihaloalkyl, perfluoroalkyl, carboxylic acid, ketone, aldehyde, nitrate, cyano, isocyanate, hydroxyl, ester, ether, amine, imine, amide, halogen-substituted amide, trifluoroamide, sulfide, disulfide, sulfonate, carbamate, silane, siloxane, phosphine, phosphate, or borate, wherein any combination of $R^5$, $R^6$, $R^7$, and $R^8$ can be linked to form one or more cyclic groups;

n is 1 or 2, such that n is 1 for the divalent heteroatoms O or S, and n is 2 for the trivalent heteroatoms N or P; and Z is selected from hydrogen, alkyl, aryl, functionalized alkyl, or functionalized aryl wherein the functional group(s) may independently comprise one or more or the following: alkoxy, aryloxy, halogen, carboxylic acid, ketone, aldehyde, nitrate, cyano, isocyanate, hydroxyl, ester, ether, amine, imine, amide, trifluoroamide, sulfide, disulfide, carbamate, silane, siloxane, phosphine, phosphate, or borate; methyl, isopropyl, sec-butyl, t-butyl, neopentyl, benzyl, phenyl and trimethylsilyl; and wherein any combination or combinations of $X^1$, $R^1$, $R^2$, $L^1$, Y, Z, $R^3$, $R^4$, $R^5$, and $R^6$ are optionally linked to a support.

In other embodiments, the methods employ hindered ruthenium metathesis catalysts of the structures above, wherein $X^1$ is halide, nitrate, alkyl, aryl, alkoxy, alkylcarboxylate, aryloxy, alkoxycarbonyl, aryloxycarbonyl, arylcarboxylate, acyl, acyloxy, alkylsulfonato, arylsulfonato, alkylsulfanyl, arylsulfanyl, alkylsulfinyl, or arylsulfinyl. In other embodiments, $X^1$ is a carboxylate, nitrate, phenoxide, bromide, chloride, iodide, sulfoxide, or nitrite. Nitrate and pivalate ligands are particularly suitable embodiments for the methods.

In the carbene ligand having the structure of Formula (II), Q is a linker, typically a hydrocarbylene linker, including substituted hydrocarbylene, heteroatom-containing hydrocarbylene, and substituted heteroatom-containing hydrocarbylene linkers, wherein two or more substituents on adjacent atoms within Q may also be linked to form an additional cyclic structure, which may be similarly substituted to provide a fused polycyclic structure of two to about five cyclic groups. Q is often, although again not necessarily, a two-atom linkage or a three-atom linkage. In more particular embodiments, Q is a two-atom linkage having the structure —$CR^{11}R^{12}$—, $CR^{13}R^{14}$— or —$CR^{11}$=$CR^{13}$—, preferably —$CR^{11}R^{12}$—$CR^{13}R^{14}$, wherein $R^{11}$, $R^{12}$, $R^{13}$, and $R^{14}$ are independently hydrogen, hydrocarbyl, substituted hydrocarbyl, heteroatom-containing hydrocarbyl, substituted heteroatom-containing hydrocarbyl, or functional groups. Examples of suitable functional groups include carboxyl, $C_1$-$C_{20}$ alkoxy, $C_5$-$C_{24}$ aryloxy, $C_2$-$C_{20}$ alkoxycarbonyl, $C_5$-$C_{24}$ alkoxycarbonyl, $C_2$-$C_{24}$ acyloxy, $C_1$-$C_{20}$ alkylthio, $C_5$-$C_{24}$ arylthio, $C_1$-$C_{20}$ alkylsulfonyl, and $C_1$-$C_{20}$ alkylsulfinyl, optionally substituted with one or more moieties selected from $C_1$-$C_{12}$ alkyl, $C_1$-$C_{12}$ alkoxy, $C_5$-$C_{14}$ aryl, hydroxyl, sulfhydryl, formyl, and halide. $R^{11}$, $R^{12}$, $R^{13}$, and $R^{14}$ are preferably independently selected from hydrogen, $C_1$-$C_{12}$ alkyl, substituted $C_1$-$C_{12}$ alkyl, $C_1$-$C_{12}$ heteroalkyl, substituted $C_1$-$C_{12}$ heteroalkyl, phenyl, and substituted phenyl. Alternatively, any two of $R^{11}$, $R^{12}$, $R^{13}$ and $R^{14}$ may be linked together to form a substituted or unsubstituted, saturated or unsaturated ring structure, e.g., a $C_4$-$C_{12}$ alicyclic group or a $C_5$ or $C_6$ aryl group, which may itself be substituted, e.g., with linked or fused alicyclic or aromatic groups, or with other substituents. In one further aspect, any one or more of $R^{11}$, $R^{12}$, $R^{13}$, and $R^{14}$ comprises one or more of the linkers.

In certain embodiments, $R^1$ is an optionally substituted alkylene, optionally substituted heteroatom-containing alkylene, optionally substituted cycloalkylene, optionally substituted heteroatom-containing cycloalkylene, optionally substituted aryl, or optionally substituted heteroaryl. In other embodiments, $R^1$ is an optionally substituted cycloalkylene or optionally substituted aryl. $R^1$ may also be an optionally substituted adamantylene group or a substituted $C_3$-$C_{12}$ cycloalkylene group. Adamantylene is a particularly suitable $R^1$ moiety.

In still other embodiments, $R^1$ is an optionally substituted cycloalkyne, an optionally substituted heteroatom-containing cycloalkylene, an optionally substituted aryl, or an optionally substituted heteroaryl and $R^2$ is an optionally substituted cycloalkyl, an optionally substituted heteroatom-containing cycloalkyl, an optionally substituted aryl, or an optionally substituted heteroaryl. Further embodiments provide that $R^1$ is an optionally substituted cycloalkylene and $R^2$ is a substituted aryl group. When $R^2$ is a substituted aryl group, certain embodiments provide that one or both ortho positions are substituted, preferably by methyl, ethyl, propyl, or isopropyl substitutents. Under these conditions, the other meta or para-positions may also be substituted. Suitable substituent patterns include those where $R^2$ is 2,4,6-trimethyl phenyl (mesityl), methylisopropylphenyl (MIPP), or di-isopropylphenyl (DIPP).

Good results have been obtained in those embodiments where Q is an optionally substituted ethylene (—$CH_2CH_2$—), $R^1$ is an optionally substituted adamantylene, $R^2$ is 2,4,6-trimethyl phenyl (mesityl), 2-methyl-6-isopropylphenyl (MIPP), or 2,6-di-isopropylphenyl (DIPP); $X^1$ is nitrate or pivalate, $R^3$, $R^4$, $R^5$, and $R^6$ are each hydrogen; Y is O; and $(Z)_n$ is isopropyl.

Without intending to be bound by the correctness or incorrectness of any theory, it appears that the selectivity exhibited by these catalysts in the present applications arises from the steric effects of the bulky chelated carbene moiety bound to the ruthenium atom. The effects of the steric bulk of ligands on organometallic compounds generally, and those containing imidazolinyl ligands in particular, have discussed in a parameter known as "percent buried volume." This concept which describes the steric pressure brought about by the use of NHC ligands has been recently summarized in H. Clavier and S. P. Nolan, Chem. Comm., 2010, 46, 841-861. In the present methods, it appears that the greater the steric effect of the carbene described above, the more selective is the catalyst in forming Z-olefins. Accordingly, certain embodiments provide for methods where the percent volume buried by the carbene moiety is greater than about 45%. In other embodiments, the percent volume buried is greater than about 50%. For the purposes of the present invention, the percent buried volume is calculated based on an M-NHC bond length of 2.00 Å (as described in the Calvier and Nolan paper above).

Accordingly, suitable C—H activated olefin metathesis catalyst compound comprise one or more of the following:

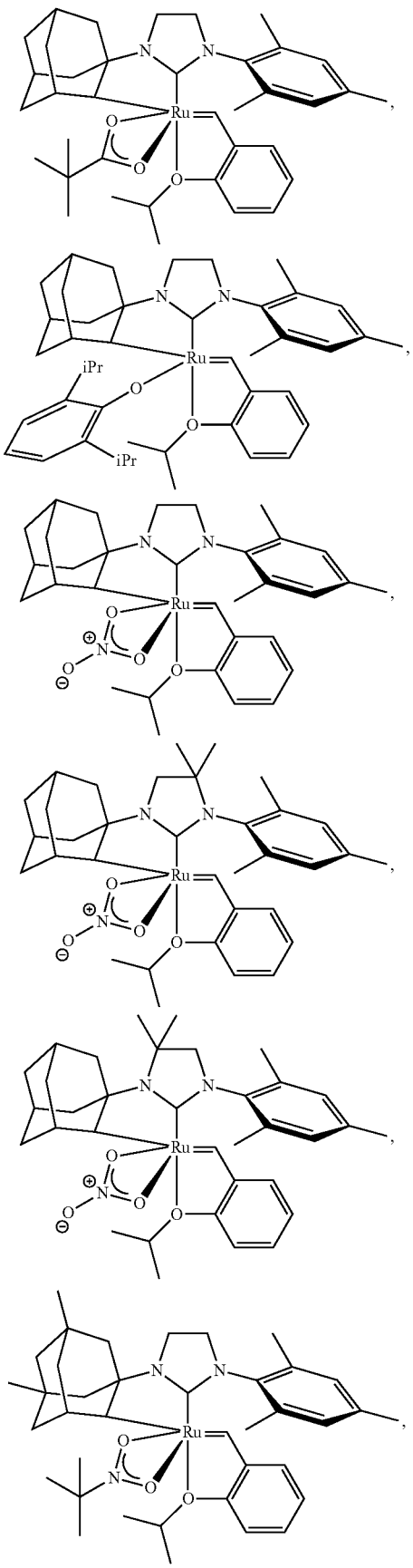

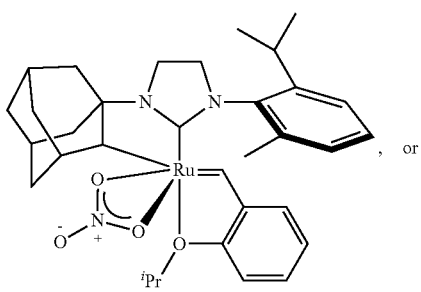

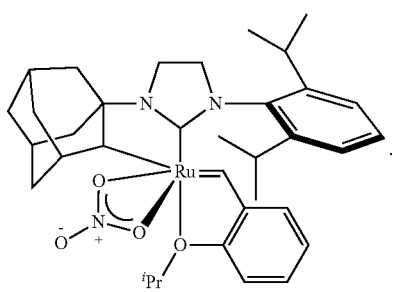

More specific embodiments include those where the C—H activated olefin metathesis catalyst compound comprises one or more of the following structures:

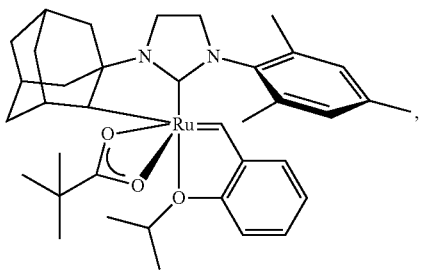

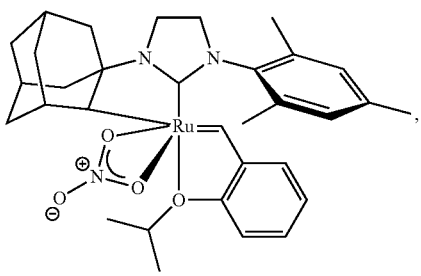

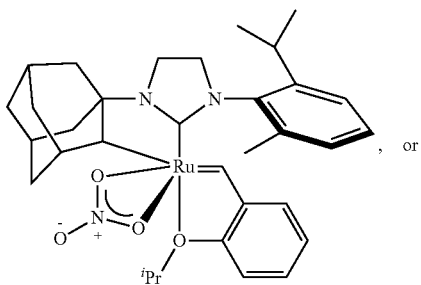

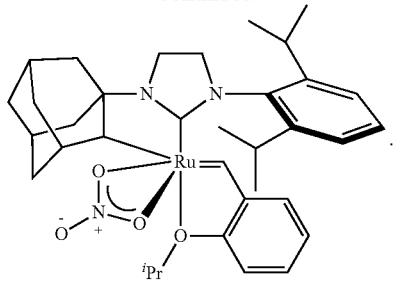

As described above, the methods of the present invention include those methods of synthesizing a Z-olefin metathesis product, each method comprising: (a) cross-metathesizing (i) a terminal olefin and an internal olefin or (ii) two terminal olefins in the presence of a hindered ruthenium metathesis catalyst to form the Z-olefin metathesis product and a side product. The cross-metathesis of the (i) terminal olefin and an internal olefin and the (ii) two terminal olefins are obviously independent embodiments. Recognizing that the entire concept of olefin metathesis provides that, in addition to the desired product, the reaction scheme provides for at least one co-product or side product. However, it should also be appreciated that the reaction also provides for some extraneous reaction products, which may include additional side- or by-products arising, for example, from the homo-dimerization or solvolysis of the initial substrates, intermediates, or final products. Therefore, in this specification, a reference to "a side product" should not be interpreted as indicating that the reaction necessarily provides a single side product, so much as to refer to the product which forms according to the nominal stoichiometry of the metathesis. Typically, but not always, the starting materials are chosen to provide that the side product comprises a $C_2$-$C_{10}$ olefin. Note that if the side-product is low boiling relative to the reaction solvent or starting or product materials, as in the case of ethylene or propylene, the natural evolution of the side product drives the reaction to form the desired product.

An attractive feature of the methods described herein is the mild conditions under which the metatheses may be conducted. For example, the metathesis reaction may be conducted at at least one temperature in a range of from about 18° C. to about 200° C. Additional embodiments provide that the reactions are conducts in a range having a lower limit of about 0° C., about 10° C., about 20° C., about 30° C., about 40° C., about 50° C., about 60° C., about 70° C., or about 80° C. and having an upper limit of about 200° C., about 175° C., about 150° C., about 125° C., or about 100° C., with exemplary ranges also including temperatures in a range of from about 40° C. to about 100° C., or from about 50° C. to about 80° C. In some cases, higher yields and/or selectivity may be achieved at higher temperatures in these ranges; in other cases, higher yields and/or selectivity may be achieved at lower temperatures in these ranges. The skilled artisan would be able to optimize both, without undue experimentation. Further, exemplary reaction times are in a range of from about 10-30 minutes to about 120 hours, depending on the choice of catalyst, starting materials, and operating temperatures and pressures. Again, it would be within the skill of the ordinary skilled artisan to optimize reaction conditions, without undue experimentation. Within these parameters, it is not uncommon to achieve turnover numbers exceeding 500, 1000, 2000, or even 5000 based on starting materials.

Following the cross-metathesis reactions, the invention also provides for the isolation of the desired product and the optional further reaction thereto. The isolation and/or purification of the desired Z-olefin product may comprise applying conditions sufficient to remove the desired metathesis product from the side product, residual starting materials, and other components of the metathesis reaction medium. This may be achieved, for example, by (a) providing sufficiently high temperature (e.g., above about 50° C., about 75° C., about 100° C., about 125° C., about 150° C., or above about 200° C.) or sufficiently low pressure (e.g., less than ambient atmospheric pressure, or less than about 700 mm Hg, about 600 mm Hg, about 500 mm Hg, about 400 mm Hg, about 300 mm Hg, about 200 mm Hg, about 100 mm Hg, about 50 mm Hg, about 25 mm Hg, or less than about 10 mm Hg), or both, so as to preferentially volatilize the side product from the metathesis product, or vice versa (i.e., distillation); (b) extracting the side product from the metathesis product with a solvent; or (c) chromatographic methods (e.g., by various liquid or gas chromatographic methods). The choice of method, obviously, depends on the specific starting materials and products, and it would be well within the skill of the ordinary artisan to devise purification schemes suitable for the specific chemistries.

The hindered ruthenium catalysts allow for the metatheses of an extremely wide range of substrates, particularly those where the initial terminal olefin has a —CH=CH$_2$ motif and the internal olefin has a —CH=CH— motif. For example, the methods are suitable when at least one of the starting olefins comprises an alkene which contains 2-44 carbons, alkenyl ester which contains 2 to 22 carbons; alkenyl halide which contains 2 to 22 carbons; alpha,omega-alkenyl diester which contains 4 to 40 carbons; alpha,omega-alkenyl dihalide which contains 4 to 40 carbons; alkenol which contains 2 to 22 carbons; alkene diol of which contains 4 to 40 carbons; or a derivative thereof. When described as such, additional embodiments include those in which at least one of the starting olefins comprises an alkenyl ester which contains 2 to 10 carbons; alkenyl halide which contains 2 to 10 carbons; alpha, omega-alkenyl diester which contains 4 to 20 carbons; alpha, omega-alkenyl dihalide which contains 4 to 20 carbons; alkene of which contains 2 to 20 carbons; alkenol which contains 2 to 10 carbons; alkene diol of which contains 4 to 20 carbons; or a derivative thereof. Methods employing the use of derivatives of fatty acids (e.g., oleyl alcohol or 11-eicosenol or their derivatives) are specific embodiments.

Other embodiments can be stated in terms of methods of cross-metathesizing (i) a terminal olefin and an internal olefin or (ii) two terminal olefins in the presence of a hindered ruthenium metathesis catalyst to form the Z-olefin metathesis product, wherein at least one of the starting olefins comprises a terminal or internal olefin optionally comprising at least one aldehyde, amino, amide, hydroxyl or protected hydroxyl, branched alkyl, alkylaryl, alkylheteroaryl, $C_{1-6}$ alkenyl, $C_{1-6}$ alkynyl, $C_{1-6}$ alkoxy, azide, —N—C(O)—$C_{1-6}$ alkyl, —O—C(O)—$C_{1-6}$ alkyl, —N—C(O)—O—$C_{1-6}$ alkyl, —O—C(O)—O—$C_{1-6}$ alkyl, aryl, carboxylic acid, carboxy ester, cyano, epoxide, fluorinated or perfluorinated alkyl, halo (fluorine, chloro, bromo, iodo), heterocyclyl, heteroaryl, or ketone. Within these general classes of compounds suitable for the inventive cross-metatheses, exemplary compounds include, but are not limited to allyl acetate, allyl bromide, allyl chloride, 2-(allyloxy)ethanol, 1-propene, 2-propyl acetate, 2-propyl bromide, 2-propyl chloride, 1-butene, 3-buten-1-ol, 3-butenylacetate, 3-butenylbromide, 3-butenylchloride, 3-butenyliodide, 3-butene, 2-buten-1-ol, 2-butenylacetate, 2-butenylbromide, 2-butenylchloride, 2-butenyliodide, 1-pentene, 4-pentenol, 4-pentenyl acetate, 4-pentenyl bromide, 4-pentenyl chloride, 4-pentenyl iodide, 1-hexene, 3-hexene, trans-1,4-hexadiene, 5-hexen-1-ol, 5-hexenyl acetate, 5-hexenyl bromide, 5-hexenyl chloride, 5-hexenyl iodide, 3-hexenol, 3-hexenyl acetate, 1-bromo-3-hexene, 1-chloro-3-hexene, 1-heptene, 1-octene, 1-nonene, 5-decene, 58-nonen-1-ol, 8-nonen-1-yl acetate, 8-nonen-1-yl bromide, 8-nonen-1-yl chloride, 8-nonen-1-yl iodide, 1-dodecene, oleyl alcohol (cis-9-octadecen-1-ol), oleyl acetate (cis-9-octadecen-1-yl acetate), oleyl bromide (cis-9-octadecen-1-yl bromide), oleyl chloride (cis-9-octadecen-1-yl chloride), oleyl iodide (cis-9-octadecen-1-yl iodide), elaidyl alcohol (9E-octadecen-1-ol), elaidyl acetate (9E-octadecen-1-yl acetate), 11-docosene, 10-methyl undecenoate, 11-eicosenol, methyl 5-eicosenoate, 5-eicosneyl acetate, methyl 11-eicosenoate, 11-eicosenyl acetate, palmitoleyl alcohol (cis-9-hexadecen-1-ol), erucyl alcohol (cis-13-docosen-1-ol), erucyl acetate, erucyl bromide, or erucyl chloride.

Figure 2:
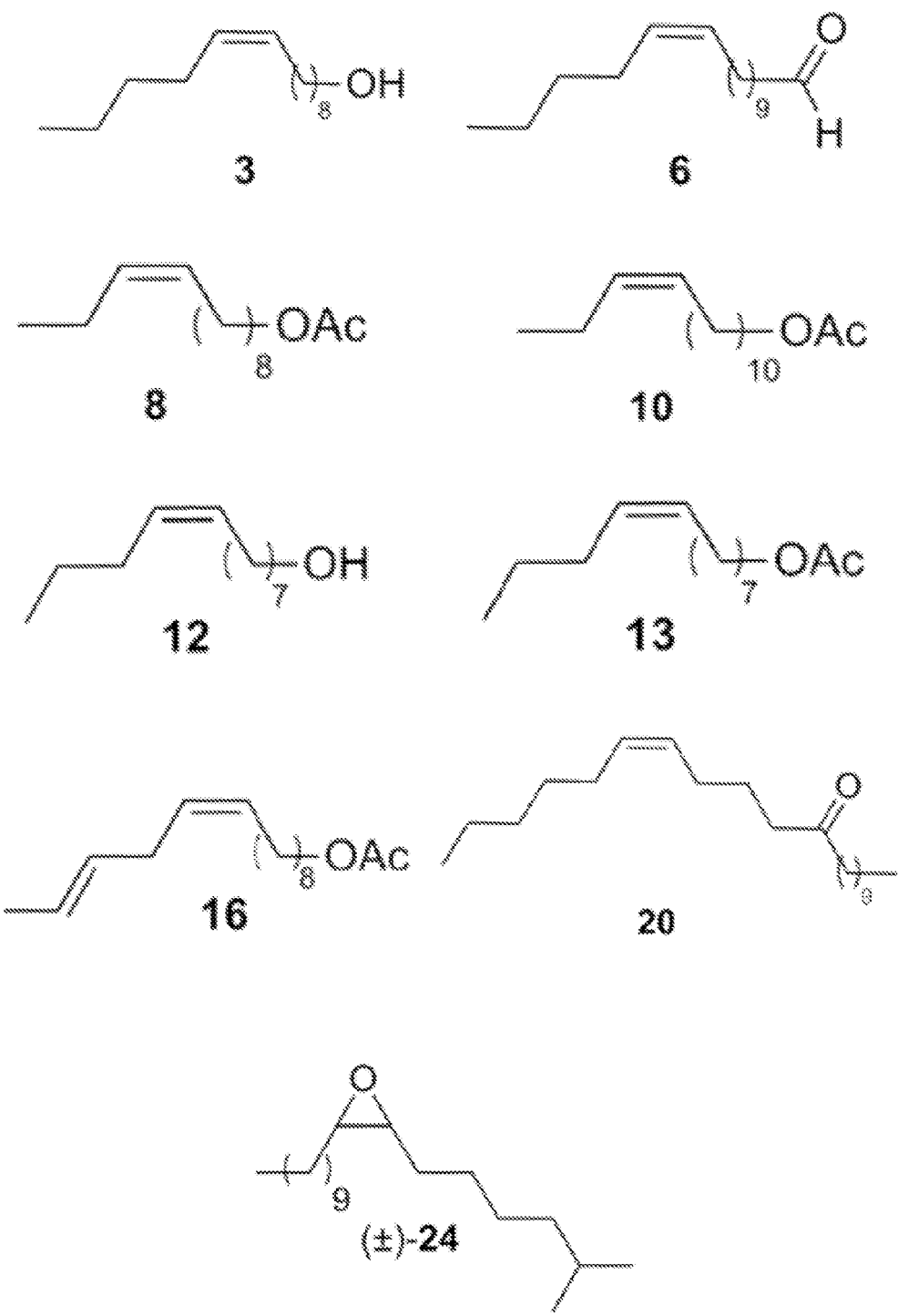
FIG. 2 provides a listing of lepidopteran insect pheromones approved for use by the EPA.
Figure 3:
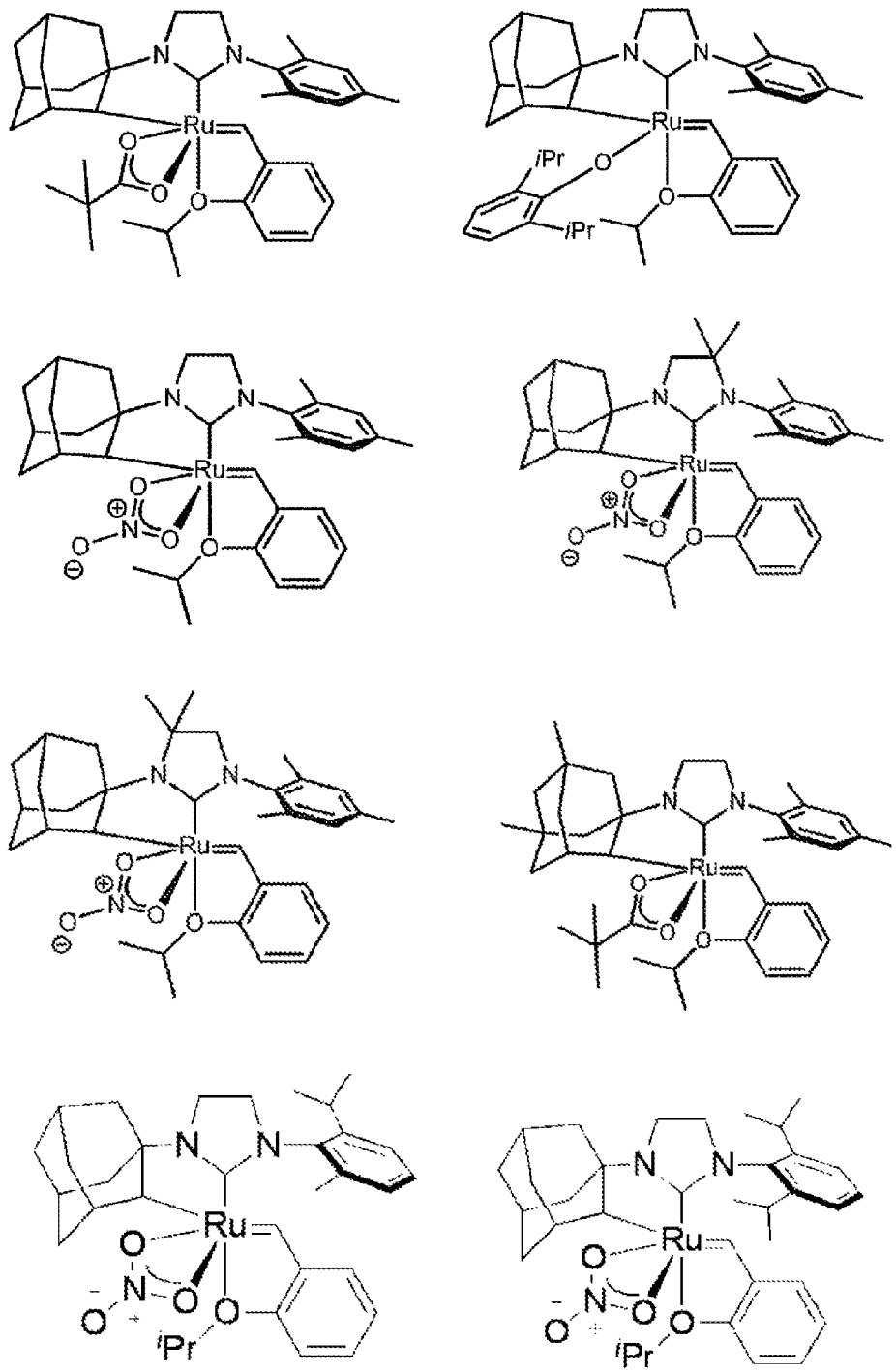
FIG. 3 depicts a range of hindered ruthenium metathesis catalysts useful in this invention.

The methods of the present invention are particularly useful for preparing a wide range of insect pheromones, including lepidopteran insect pheromones like those already approved by the U.S. Environmental Protection Agency such as are shown in FIG. 2. Accordingly, specific embodiments provide for methods wherein the metathesis product comprises a compound having the formula: 3, 5-10, 12-13, 15-17, 19-22, or 24:

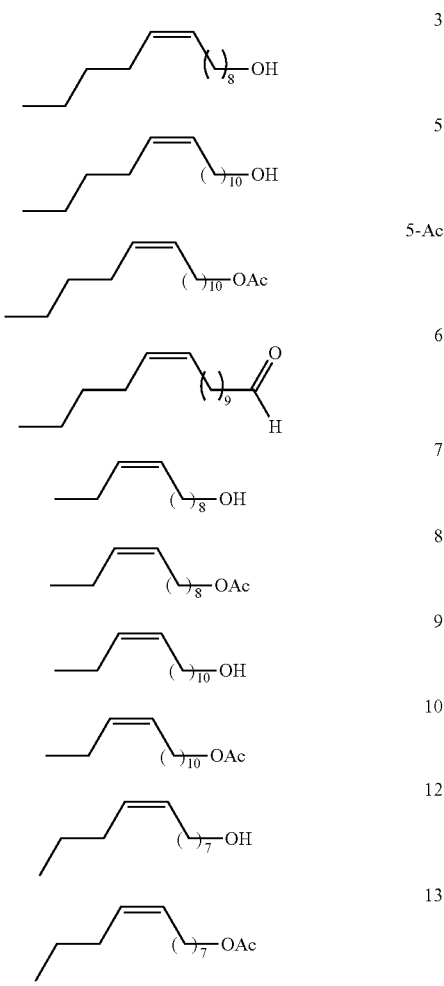

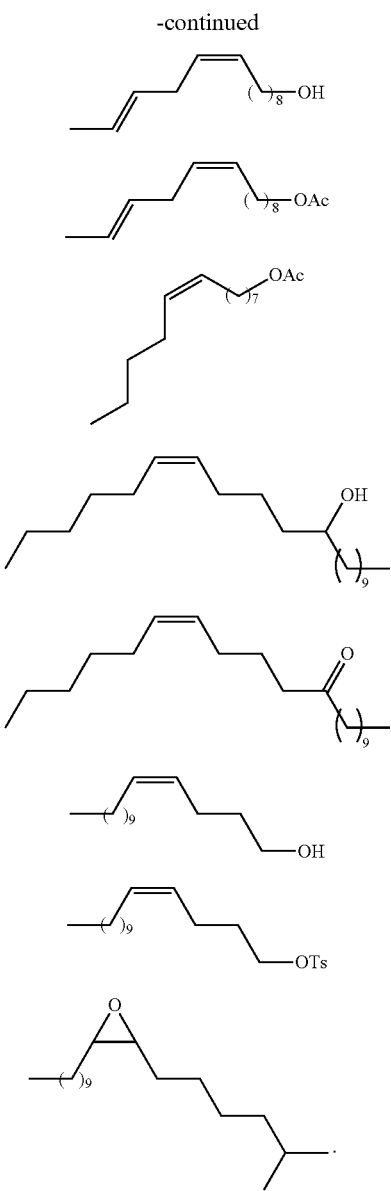

Exemplary Z-selective metathesis reactions of the seed oil derivatives, oleyl alcohol and 11-eicosenol, with 1-butene and 1-hexene can provide for the synthesis of one EPA-approved pheromone (3) and three precursors that can be converted to the corresponding pheromones (6, 8, 10) by acetylation or oxidation. Reaction of oleyl alcohol with trans-1,4-hexadiene can provide for the selective formation of a diene pheromone precursor that can be converted to (Z,E)-9,12-tetradecadienyl acetate (16) by acetylation. This appears to be the first example of a completely selective synthesis of unactivated, unconjugated dienes containing 1,2-disubstituted olefins using olefin metathesis, and this ability (i.e., to selectively metathesize terminal olefins in the presence of other unactivated, unconjugated dienes containing 1,2-disubstituted olefins) is considered to be separate embodiment of this invention. 8-nonenol was reacted with 1-pentene in a metathesis reaction catalyzed by the inventive hindered ruthenium catalysts to generate two additional EPA-approved pheromones (12,13). In addition, the alkene precursors leading to the ketone (20) and epoxide (24) substituted pheromones were also synthesized via a Z-selective metathesis reaction. The schemes for these reactions and exemplary reaction conditions are provided in the Examples below.

In some embodiments, the reaction between 1-hexene and 8-nonenyl acetate to form (Z)-tridec-8-en-1-yl acetate may be specifically excluded from any genus or sub-genus of combination of reactants and products otherwise described.

The metathesis reactions provide high yields (depending on the specific reactants, exceeding about 50%, about 60%, about 70%, about 80%, about 90%, about 95%, or even about 99%) that are highly selective for the Z-olefin (cis-isomer) and specific embodiments provide that the cis:trans isomeric ratio of the Z-olefin metathesis product is greater than about 70:30. Other independent embodiments provide that this isomeric ratio is greater than about 80:20, greater than about 90:10, greater than about 95:5, or greater than about 99:1.

Certain specific embodiments provide various methods for providing insect pheromones, the methods comprising cross-metathesizing:

(a) oleyl alcohol and 1-hexene in the presence of a hindered ruthenium metathesis catalyst to form (Z)-tetradec-9-en-1-ol (3) and 1-decene;

(b) 11-eicosenol and 1-hexene in the presence of a hindered ruthenium metathesis catalyst to form (Z)-hexadec-11-en-1-ol (5) and 1-decene; the (Z)-hexadec-11-en-1-ol (5) is optionally separated rom the 1-decene, and further oxidized to form (Z)-hexadec-11-enal (6).

(c) oleyl alcohol and 1-butene in the presence of a hindered ruthenium metathesis catalyst to form (Z)-dodec-9-en-1-ol (7) and 1-decene; the (Z)-dodec-9-en-1-ol (7) is optionally separated from the 1-decene, and acetylated to form (Z)-dodec-9-en-1-yl acetate (8);

(d) 11-eicosenol and 1-butene in the presence of a hindered ruthenium metathesis catalyst to form (Z)-tetradec-11-en-1-ol (9) and 1-decene; the (Z)-tetradec-11-en-1-ol (9) is optionally separated from the 1-decene, and acetylated to form (Z)-tetradec-11-en-1-yl acetate (10);

(e) 8-nonenol and 1-pentene in the presence of a hindered ruthenium metathesis catalyst to form (Z)-dodec-8-en-1-ol (12) and ethylene; the (Z)-dodec-8-en-1-ol (12) is optionally separated from the ethylene and acetylated to form (Z)-dodec-8-en-1-yl acetate (13);

(f) 8-nonenyl acetate and 1-pentene in the presence of a hindered ruthenium metathesis catalyst to form (Z)-dodec-8-en-1-yl acetate (13) and ethylene;

(g) oleyl alcohol and 1,4-trans-hexadiene in the presence of a hindered ruthenium metathesis catalyst to form (9Z,12E)-tetradeca-9,12-dien-ol (15) and 1-decene; the (9Z,12E)-tetradeca-9,12-dien-ol (15) is optionally separated from the 1-decene, and acetylated to form (9Z,12E)-tetradeca-9,12-dien-yl acetate (16);

(h) 1-hexene and 8-nonenyl acetate to form (Z)-tridec-8-en-1-yl acetate (17) and ethylene;

(i) (Z)-hexadec-1-6-ol and 1-heptene to form (Z)-henicos-6-en-11-ol (19) and ethylene; the (Z)-henicos-6-en-11-ol (19) is optionally separated from the ethylene, and oxidized to form (Z)-henicos-6-en-11-one (20);

(j) 4-pentanol and 1-dodecene in the presence of a hindered ruthenium metathesis catalyst to form (Z)-pentadec-4-en-1-ol (21) and ethylene.

If not already mentioned herein, it should be apparent that this invention also includes those embodiments where the cross-metathesis product may be further reacted to form at least simple derivatives therefrom. For example, alcohol, carboxylate ester (in addition to, or including acetate esters), and halide functional groups may be interconverted using standard organic chemistry methodologies. Also, for example, the schemes and methods used to convert, for example, (Z)-pentadec-4-en-1-ol (21) to (Z)-pentadecen-4-en-1-yl 4-methylbenzenesulfonate (22) and cis-7,8-epoxy-2-methyloctadecane ((±)-24) are also considered within the scope of the present invention.

In these methods, certain specific embodiments provide that the hindered ruthenium metathesis catalyst comprises at least one of the following:

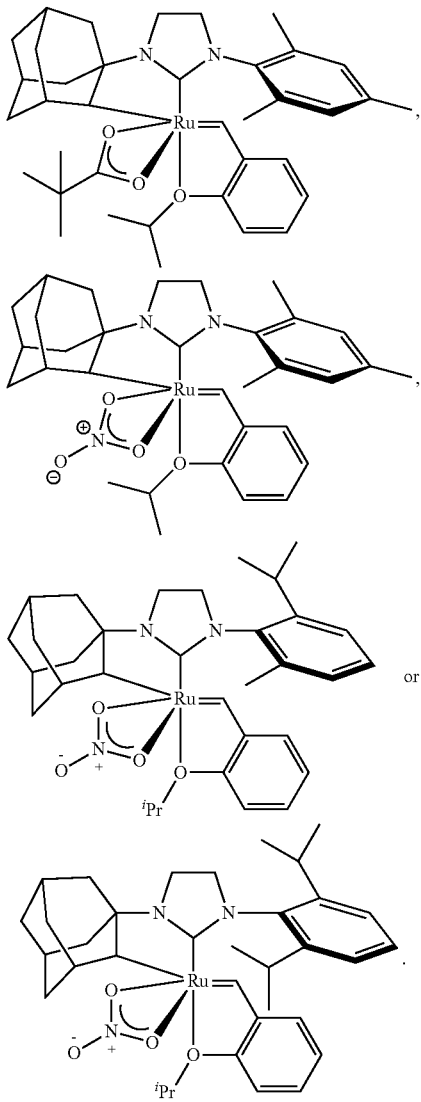

The two ruthenium catalysts listed as 1 and 9 are individually preferred:

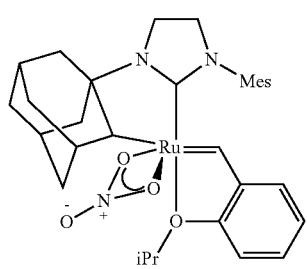

1

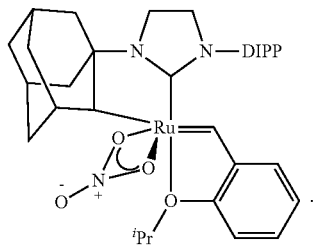

9

While most of the discussion to this point has centered on the coupling of metathesis of two starting materials to form a Z-olefin and a separate side product, it should also be apparent that the choice of starting olefins is not constrained to individual olefin compounds so as to yield acyclic products. Rather, the (i) a terminal olefin and an internal olefin or (ii) two terminal olefins may be present within a single larger compound, in which case, the metathesis may provide a macrocyclic Z-olefin compound. Similarly, the use of di-olefin starting materials may also provide for polymers comprising the cis-olefin geometries.

The following listing of embodiments in intended to complement, rather than displace or supersede, any of the previous descriptions.

Item 1. A method of synthesizing a Z-olefin metathesis product, said metathesis product being a moiety within a cyclic or acyclic insect pheromone or a cyclic or acyclic lepidopteran insect pheromone, said method comprising:

(a) cross-metathesizing (i) a terminal olefin and an internal olefin or (ii) two terminal olefins in the presence of a hindered ruthenium metathesis catalyst to form the insect pheromone containing Z-olefin metathesis product and a side product;

the hindered metathesis catalyst comprising a C—H activated olefin metathesis catalyst compound having a structure of Formula I:

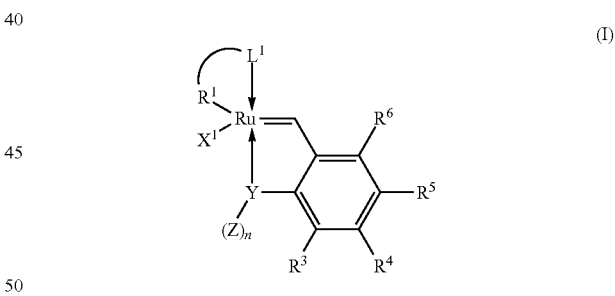

(I)

wherein
$X^1$ is an anionic ligand;
$L^1$ is a carbene ligand having the structure of Formula (II):

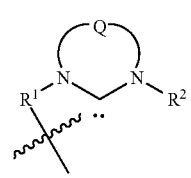

(II)

wherein,
Q is selected from hydrocarbylene, substituted hydrocarbylene, heteroatom-containing hydrocarbylene, or substituted heteroatom-containing hydrocarbylene, wherein two or more substituents on adjacent atoms within Q may also be linked to form an additional cyclic structure;

$R^1$ is an optionally substituted hydrocarbylene or an optionally substituted heteroatom-containing hydrocarbylene, where $R^1$ links $L^1$ and M and, together with $L^1$ and M, form one or more cyclic groups, and wherein M, $L^1$ and $R^1$ form an M-$R^1$-$L^1$ chelating ligand ring structure having a ring size of 5, 6, or 7 atoms;

$R^2$ is an optionally substituted hydrocarbyl or an optionally substituted heteroatom-containing hydrocarbyl'

Y is N, O, S, or P;

$R^3$, $R^4$, $R^5$, and $R^6$ are each, independently, hydrogen, halogen, alkyl, alkenyl, alkynyl, aryl, heteroalkyl, heteroatom containing alkenyl, heteroalkenyl, heteroaryl, alkoxy, alkenyloxy, aryloxy, alkoxycarbonyl, carbonyl, alkylamino, alkylthio, aminosulfonyl, monoalkylaminosulfonyl, dialkylaminosulfonyl, alkylsulfonyl, nitrile, nitro, alkylsulfinyl, trihaloalkyl, perfluoroalkyl, carboxylic acid, ketone, aldehyde, nitrate, cyano, isocyanate, hydroxyl, ester, ether, amine, imine, amide, halogen-substituted amide, trifluoroamide, sulfide, disulfide, sulfonate, carbamate, silane, siloxane, phosphine, phosphate, or borate, wherein any combination of $R^5$, $R^6$, $R^7$, and $R^8$ can be linked to form one or more cyclic groups;

n is 1 or 2, such that n is 1 for the divalent heteroatoms O or S, and n is 2 for the trivalent heteroatoms N or P; and Z is selected from hydrogen, alkyl, aryl, functionalized alkyl, or functionalized aryl wherein the functional group(s) may independently comprise one or more or the following: alkoxy, aryloxy, halogen, carboxylic acid, ketone, aldehyde, nitrate, cyano, isocyanate, hydroxyl, ester, ether, amine, imine, amide, trifluoroamide, sulfide, disulfide, carbamate, silane, siloxane, phosphine, phosphate, or borate; methyl, isopropyl, sec-butyl, t-butyl, neopentyl, benzyl, phenyl and trimethylsilyl; and wherein any combination or combinations of $X^1$, $R^1$, $R^2$, $L^1$, Y, Z, $R^3$, $R^4$, $R^5$, and $R^6$ are optionally linked to a support.

Item 2. The method of item 1, wherein $X^1$ is halide, nitrate, alkyl, aryl, alkoxy, alkylcarboxylate, aryloxy, alkoxycarbonyl, aryloxycarbonyl, arylcarboxylate, acyl, acyloxy, alkylsulfonato, arylsulfonato, alkylsulfanyl, arylsulfanyl, alkylsulfinyl, or arylsulfinyl.

Item 3. The method of item 2, wherein $X^1$ is a carboxylate, nitrate, phenoxide, bromide, chloride, iodide, sulfoxide, or nitrite.

Item 4. The method of any of the preceding items, wherein $R^1$ is an optionally substituted alkylene, optionally substituted heteroatom-containing alkylene, optionally substituted cycloalkylene, optionally substituted heteroatom-containing cycloalkylene, optionally substituted aryl, or optionally substituted heteroaryl.

Item 5. The method of item 4, wherein $R^1$ is an optionally substituted cycloalkylene or optionally substituted aryl.

Item 6. The method of any of the preceding items, wherein $R^1$ is an optionally substituted cycloalkylene, an optionally substituted heteroatom-containing cycloalkylene, an optionally substituted aryl, or an optionally substituted heteroaryl and $R^2$ is an optionally substituted cycloalkyl, an optionally substituted heteroatom-containing cycloalkyl, an optionally substituted aryl, or an optionally substituted heteroaryl.

Item 7. The method of any of the preceding items, wherein $R^1$ is an optionally substituted cycloalkylene and $R^2$ is a substituted aryl group.

Item 8. The method of any of the preceding items, wherein $R^1$ is an optionally substituted adamantylene group or a substituted $C_3$-$C_{12}$ cycloalkylene group.

Item 9. The method of item 6 or 7, wherein $R^2$ is a substituted aryl group in which both ortho rings are substituted.

Item 10. The method of any one of the preceding items, wherein Q is an optionally substituted ethylene (—$CH_2CH_2$—), $R^1$ is an optionally substituted adamantylene, $R^2$ is 2,4,6-trimethyl phenyl (mesityl), methylisopropylphenyl (MIPP), or di-isopropylphenyl (DIPP); $X^1$ is nitrate or pivalate, $R^3$, $R^4$, $R^5$, and $R^6$ are each hydrogen; Y is O; and $(Z)_n$ is isopropyl.

Item 11. The method of any one of the preceding items, wherein the percent volume buried by the carbene moiety is greater than about 45% or greater than about 50%.

Item 12. The method of any one of the preceding items, the C—H activated olefin metathesis catalyst compound comprising at least one of the following:

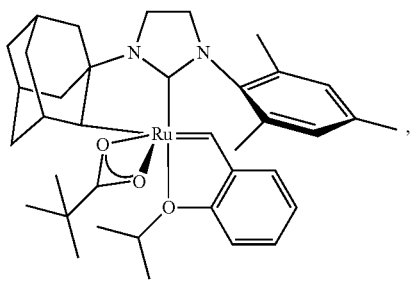

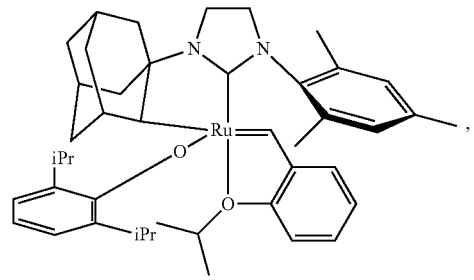

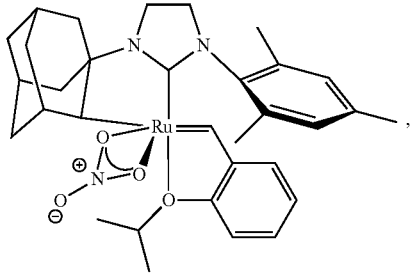

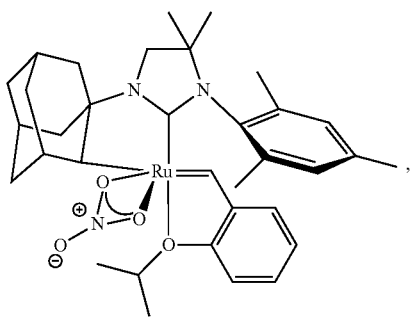

-continued

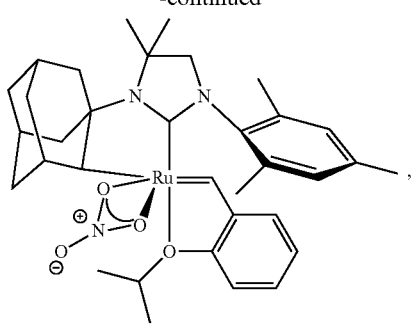

,

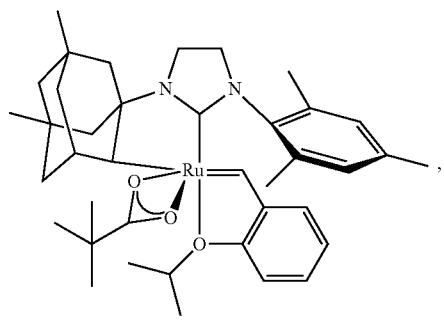

,

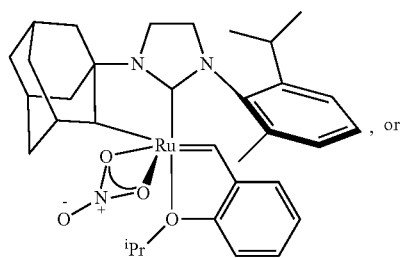

, or

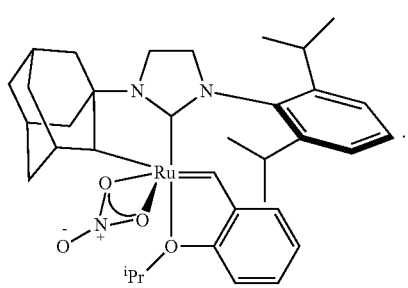

.

Item 13. The method of any one of the preceding items, the C—H activated olefin metathesis catalyst compound comprising at least one of the following:

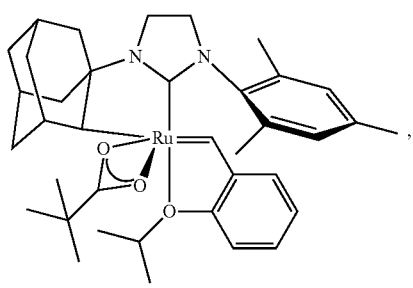

,

-continued

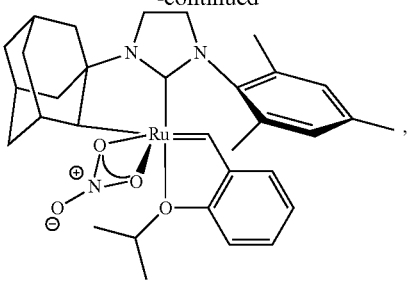

,

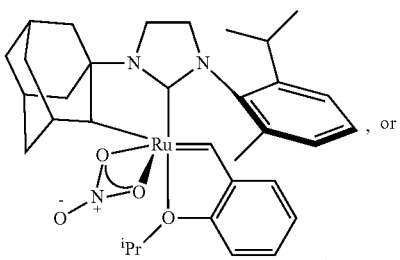

, or

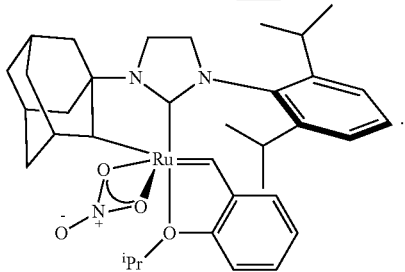

.

Item 14. The method of any one of the preceding items, further comprising (b) applying conditions sufficient to remove the side product from the metathesis product.

Item 15. The method of any one of the preceding claims, the method comprising cross-metathesizing a terminal olefin and an internal olefin.

Item 16. The method of any one of items 1 to 14, the method comprising cross-metathesizing two terminal olefins.

Item 17. The method of any one of items 2 to 16, the conditions sufficient to remove the side product from the metathesis product including (a) providing sufficiently high temperature or sufficiently low pressure, or both, so as to preferentially volatilize the side product from the metathesis product, or vice versa (i.e., distillation); (b) extracting the side product from the metathesis product with a solvent; or (c) chromatographic methods.

Item 18. The method of any one of items 14 to 17, the method comprising applying the conditions sufficient to remove the side product from the metathesis product during the cross-metathesis reaction.

Item 19. The method of any one of the preceding items, wherein at least one of the starting olefins comprises an alkenyl ester which contains 2 to 22 carbons; alkenyl halide which contains 2 to 22 carbons; alpha,omega-alkenyl diester which contains 4 to 40 carbons; alpha,omega-alkenyl dihalide which contains 4 to 40 carbons; alkene which contains 2 to 44 carbons; alkenol which contains 2 to 22 carbons; alkene diol of which contains 4 to 40 carbons; or a derivative thereof.

Item 20. The method of any one of the preceding items, wherein the terminal olefin has a —CH=CH$_2$ motif and the internal olefin has a —CH=CH— motif.

Item 21. The method of any one of the preceding items, wherein at least one of the starting olefins comprises a terminal or internal olefin optionally comprising at least one aldehyde, amino, amide, hydroxyl or protected hydroxyl, branched alkyl, alkylaryl, alkylheteroaryl, $C_{1-6}$ alkenyl, $C_{1-6}$ alkynyl, $C_{1-6}$ alkoxy, azide, —N—C(O)—$C_{1-6}$ alkyl, —O—C(O)—$C_{1-6}$ alkyl, —N—C(O)—O—$C_{1-6}$ alkyl, —O—C(O)—O—$C_{1-6}$ alkyl, aryl, carboxylic acid, carboxy ester, cyano, epoxide, fluorinated or perfluorinated alkyl, halo (fluorine, chloro, bromo, iodo), heterocyclyl, heteroaryl, or ketone.

Item 22. The method of any one of the preceding items, wherein at least one of the starting olefins comprises allyl acetate, 2-(allyloxy)ethanol, 1-propene, 1-butene, 1-pentene, 1-hexene, 3-hexene, trans-1,4-hexadiene, 1-heptene, 1-octene, 1-nonene, 5-decene, 2-buten-1-ol, 2-butenylacetate, 2-butenylbromide, 2-butenylchloride, 2-butenyliodide, 4-pentenol, 4-pentenyl acetate, 4-pentenyl bromide, 4-pentenyl chloride, 4-pentenyl iodide, 5-hexen-1-ol, 5-hexenyl acetate, 5-hexenyl bromide, 5-hexenyl chloride, 5-hexenyl iodide, 3-hexenol, 3-hexenyl acetate, 1-bromo-3-hexene, 1-chloro-3-hexene, 8-nonen-1-ol, 8-nonen-1-yl acetate, 8-nonen-1-yl bromide, 8-nonen-1-yl chloride, 8-nonen-1-yl iodide, 1-dodecene, oleyl alcohol (cis-9-octadecen-1-ol), oleyl acetate (cis-9-octadecen-1-yl acetate), oleyl bromide (cis-9-octadecen-1-yl bromide), oleyl chloride (cis-9-octadecen-1-yl chloride), oleyl iodide (cis-9-octadecen-1-yl iodide), elaidyl alcohol (9E-octadecen-1-ol), elaidyl acetate (9E-octadecen-1-yl acetate), 11-docosene, 10-methyl undecenoate, 11-eicosenol, methyl 5-eicosenoate, 5-eicosneyl acetate, methyl 11-eicosenoate, 11-eicosenyl acetate, palmitoleyl alcohol (cis-9-hexadecen-1-ol), erucyl alcohol (cis-13-docosen-1-ol), erucyl acetate, erucyl bromide, or erucyl chloride.

Item 23. The method of any one of the preceding items, wherein the side product comprises a $C_2$-$C_{10}$ olefin.

Item 24. The method of any one of the preceding items, wherein the metathesis product comprises a compound having the formula: 3, 5-10, 12-13, 15-17, 19-22, or 24.

Item 25. The method of any one of the preceding items, wherein the metathesis product is further purified by distillation or chromatography.

Item 26. The method of any one of the preceding items, wherein the cross-metathesis reaction is conducted at at least one temperature in a range of from about 18° C. to about 200° C.

Item 27. The method of any one of the preceding items, wherein the cis:trans isomeric ratio of the Z-olefin metathesis product is greater than 70:30, greater than 80:20, greater than 90:10, greater than 95:5, or greater than 99:1.

Item 28. The method of any one of items 17 to 27, the low pressure being less than about 50 mmHg.

Item 29. The method of any of the preceding items, with the proviso that the reaction does not comprise the cross-metathesis of 1-hexene and 8-nonenyl acetate to form (Z)-tridec-8-en-1-yl acetate (17).

Item 30. The method of any one of the items 1 to 28, said method comprising cross-metathesizing oleyl alcohol and 1-hexene in the presence of the hindered ruthenium metathesis catalyst to form (Z)-tetradec-9-en-1-ol (3) and 1-decene.

Item 31. The method of any one of the items 1 to 28, said method comprising cross-metathesizing 11-eicosenol and 1-hexene in the presence of the hindered ruthenium metathesis catalyst to form (Z)-hexadec-11-en-1-ol (5) and 1-decene.

Item 32. The method of item 30, further comprising optionally separating the (Z)-hexadec-11-en-1-ol (5) from the 1-decene, and acetylating the (Z)-hexadec-11-en-1-ol (5) to form (Z)-hexadec-11-en-1-yl acetate (5-Ac).

Item 33. The method of item 32, further comprising optionally separating the (Z)-hexadec-11-en-1-ol (5) from the 1-decene, and further oxidizing the (Z)-hexadec-11-en-1-ol (5) to form (Z)-hexadec-11-enal (6).

Item 34. The method of any one of the items 1 to 28, said method comprising cross-metathesizing oleyl alcohol and 1-butene in the presence of the hindered ruthenium metathesis catalyst to form (Z)-dodec-9-en-1-ol (7) and 1-decene.

Item 35. The method of item 34, said method comprising optionally separating the (Z)-dodec-9-en-1-ol (7) from the 1-decene, and acetylating the (Z)-dodec-9-en-1-ol (7) to form (Z)-dodec-9-en-1-yl acetate (8).

Item 36. The method of any one of the items 1 to 28, said method comprising cross-metathesizing 11-eicosenol and 1-butene in the presence of the hindered ruthenium metathesis catalyst to form (Z)-tetradec-11-en-1-ol (9) and 1-decene.

Item 37. The method of item 36, further comprising optionally separating the (Z)-tetradec-11-en-1-ol (9) and 1-decene, and acetylating the (Z)-tetradec-11-en-1-ol (9) to form (Z)-tetradec-11-en-1-yl acetate (10).

Item 38. The method of any one of the items 1 to 28, said method comprising cross-metathesizing 8-nonenol and 1-pentene in the presence of the hindered ruthenium metathesis catalyst to form (Z)-dodec-8-en-1-ol (12) and ethylene.

Item 39. The method of item 38, further comprising optionally separating the (Z)-dodec-8-en-1-ol (12) and ethylene, and acetylating the (Z)-dodec-8-en-1-ol (12) to form (Z)-dodec-8-en-1-yl acetate (13).

Item 40. The method of any one of the items 1 to 28, said method comprising cross-metathesizing 8-nonenyl acetate and 1-pentene in the presence of the hindered ruthenium metathesis catalyst to form (Z)-dodec-8-en-1-yl acetate (13) and ethylene.

Item 41. The method of any one of the items 1 to 28, said method comprising cross-metathesizing oleyl alcohol and 1,4-trans-hexadiene in the presence of a hindered ruthenium metathesis catalyst to form (9Z,12E)-tetradeca-9,12-dien-ol (15) and 1-decene.

Item 42. The method of item 41, further comprising optionally separating the (9Z,12E)-tetradeca-9,12-dien-ol (15) and 1-decene, and acetylating the (9Z,12E)-tetradeca-9,12-dien-ol (15) to form (9Z,12E)-tetradeca-9,12-dien-yl acetate (16).

Item 43. The method of any one of the items 1 to 28, said method comprising cross-metathesizing (Z)-hexadec-1-6-ol and 1-heptene to form (Z)-henicos-6-en-11-ol (19) and ethylene.

Item 44. The method of item 43, further comprising optionally separating the (Z)-henicos-6-en-11-ol (19) and ethylene, and oxidizing the (Z)-henicos-6-en-11-ol (19) to form (Z)-henicos-6-en-11-one (20).

Item 45. The method of any one of the items 1 to 28, said method comprising cross-metathesizing 4-pentanol and 1-dodecene in the presence of a hindered ruthenium metathesis catalyst to form (Z)-pentadec-4-en-1-ol (21) and ethylene.

Item 46. The method of any one of items 30 to 45, the hindered ruthenium metathesis catalyst comprising either of:

Item 47. The method of any one of items 30 to 45, the hindered ruthenium metathesis catalyst comprising either of:

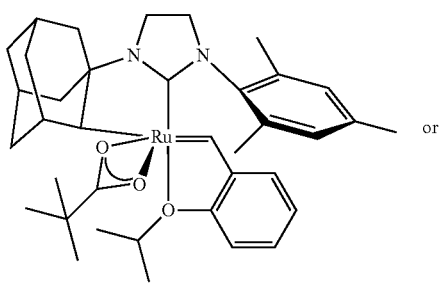

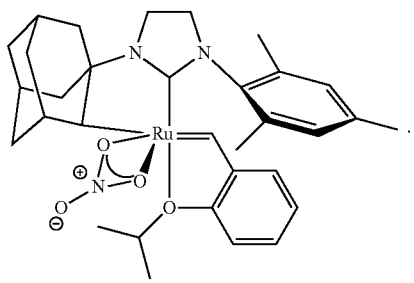

or

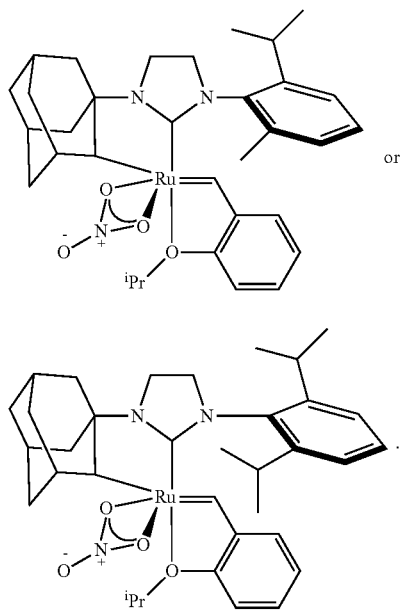

EXAMPLES

The following Examples are provided to illustrate some of the concepts described within this disclosure. While each Example is considered to provide specific individual embodiments of composition, methods of preparation and use, none of the Examples should be considered to limit the more general embodiments described herein.

General Description:

The general structures of the target cis-containing pheromones contain a single cis-1,2-disubstituted olefin that joins an unfunctionalized alkyl group to a straight chain alkyl group with a terminal functionalization (e.g., acetate, alcohol, or aldehyde) or internal functionalization (e.g., ketone, olefin). The synthetic targets depicted in FIG. 2 are all approved for use as pesticide alternatives by the EPA.

For cis-olefin containing pheromones, the starting materials are commercially available and most are commodity materials. Linear aliphatic α-olefins are produced on a large scale industrially by ethylene oligomerization by the Shell higher olefin process or the Fisher-Trope process. Oleyl alcohol and 11-eicosenol are derived from reduction of seed oil derivatives, including canola and jojoba oil. It is also suggested that two higher-cost reagents could be derived from methyl calendulate, a chemical derived from calendula oil. Ethenolysis of this species using previously reported ruthenium catalysts would yield 1-heptene (used in the synthesis of pheromone 19) and methyl-8-nonenoate, which could be subsequently reduced to yield 8-nonenol Catalysts:

In the Examples below, the catalysts referred to as "Ruthenium complex 1" or simply "1" ("Mes" is mesityl, 2,4,6-trimethylphenyl) or Ruthenium complex 9" or simply "9" ("DIPP" is 2,6-diisopropyl phenyl) are shown below:

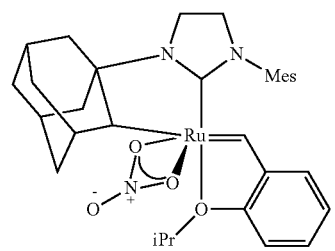

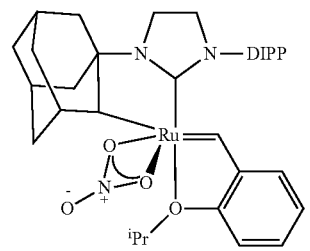

The mesityl derivatives, such as shown in Ruthenium complex 1 were prepared by methods described, for example, in co-pending application PCT/US2012/021609, using silver pivlate (AgOPiv) in THF solvent under inert atmosphere, according to a general scheme:

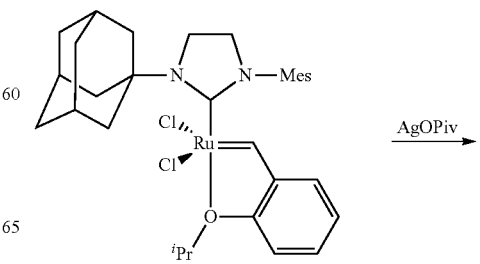

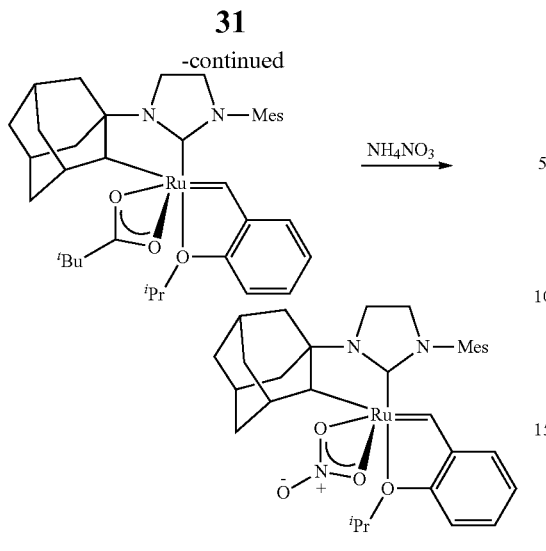

Additional compounds, as described above for the C—H activated olefin metathesis catalyst compound having a structure of Formula I, with carbene of Formula (II), where R² is 2,6,-diethyl-4-methylbenzene, 2,6,-dimethyl-4-methoxybenzene, 2,6,-dimethyl-4-chlorobenzene may also be suitable for use in the present invention, being prepared by this general scheme.

These and more sterically hindered catalysts, such as Ruthenium complex 9, and N-adamantyl-N-2,6-methylisopropylphenyl (MIPP) analogs were also prepared using a similar scheme, except using sodium pivlate (NaOPiv) in THF/methanol solvents instead of AgOPiv with the corresponding dichloro carbene precursors.

Pheromone Syntheses—General Methods:

All reactions were carried out in dry glassware under an argon atmosphere using standard Schlenk techniques or in a Vacuum Atmospheres Glovebox under a nitrogen atmosphere, unless otherwise specified. All solvents were purified by passage through solvent purification columns and further degassed by bubbling argon. NMR solvents were dried over CaH$_2$ and vacuum transferred to a dry Schlenk flask and subsequently degassed with bubbling argon. C$_6$D$_6$ was purified by passage through a solvent purification column. CDCl$_3$ was used as received. All α-olefins were filtered through a plug of neutral alumina prior to use. Ruthenium complex 1 was obtained from Materia Inc. 11-eicosenol (4) was synthesized from Jojoba oil, as described in R. L. Pederson, I. M. Fellows, T. A. Ung, H. Ishihara, S. P. Hajela, *Adv. Synth. Catal.* 2002, 344, 728. Other commercially available reagents and silica gel were used as received. ¹H NMR spectra were acquired at 500 MHz and ¹³C NMR spectra at 125 MHz as CDCl$_3$ solutions unless otherwise noted. Quantitative ¹³C measurements were acquired at 100 MHz (decoupled, without NOE, 15 second delay time). High-resolution mass spectra (HRMS) were provided by the California Institute of Technology Mass Spectrometry Facility using a JEOL JMS-600H High Resolution Mass Spectrometer. All HRMS were by positive-ion EI or FAB. All cross metathesis reactions involving the seed oil derivatives oleyl alcohol 2 and 4 required purification by multiple columns to separate the desired products from the starting material and any terminal olefins generated.

Pheromone Syntheses—Synthetic Schemes:

The following six schemes provide an overview of the Examples cited herein.

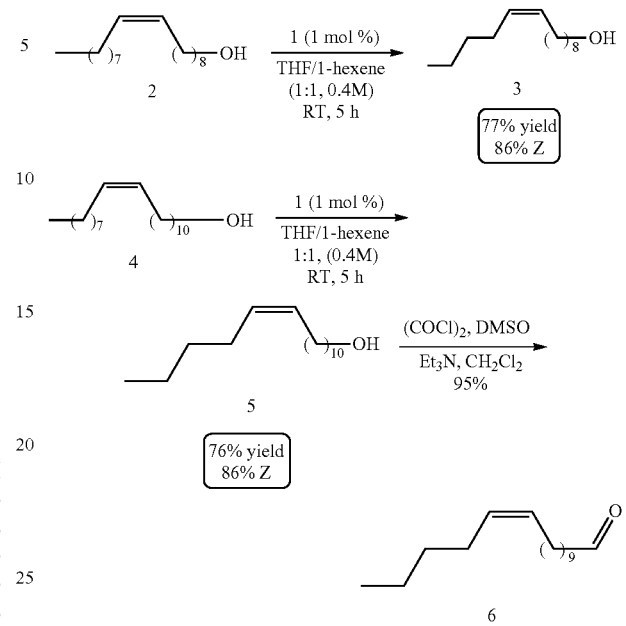

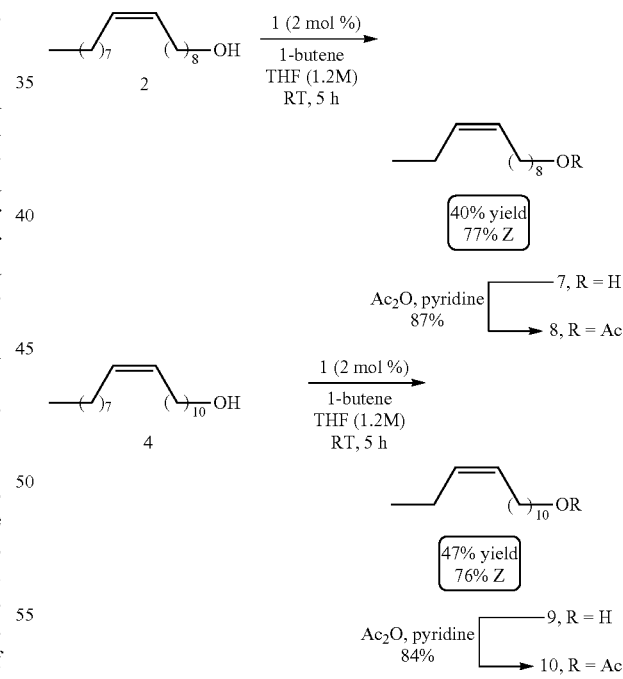

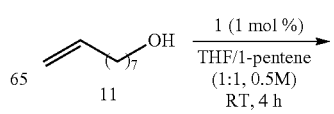

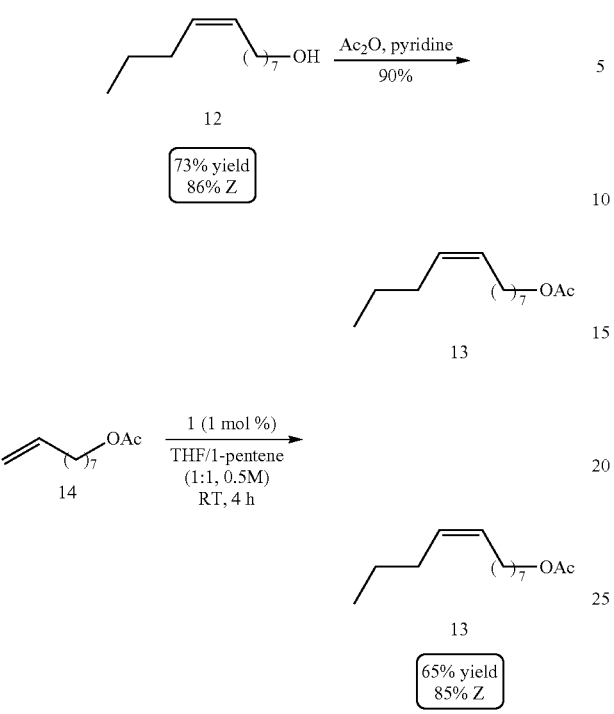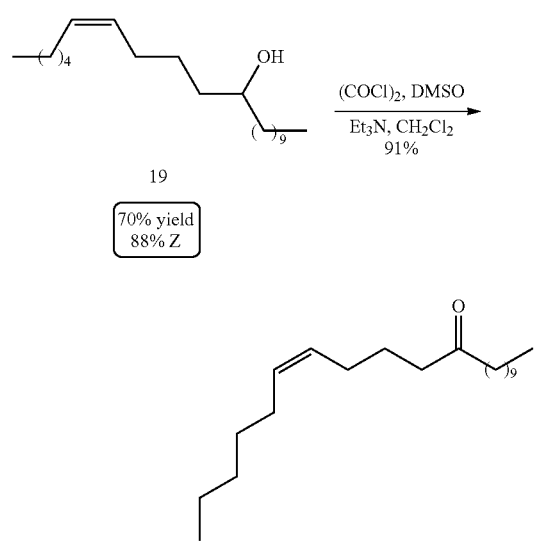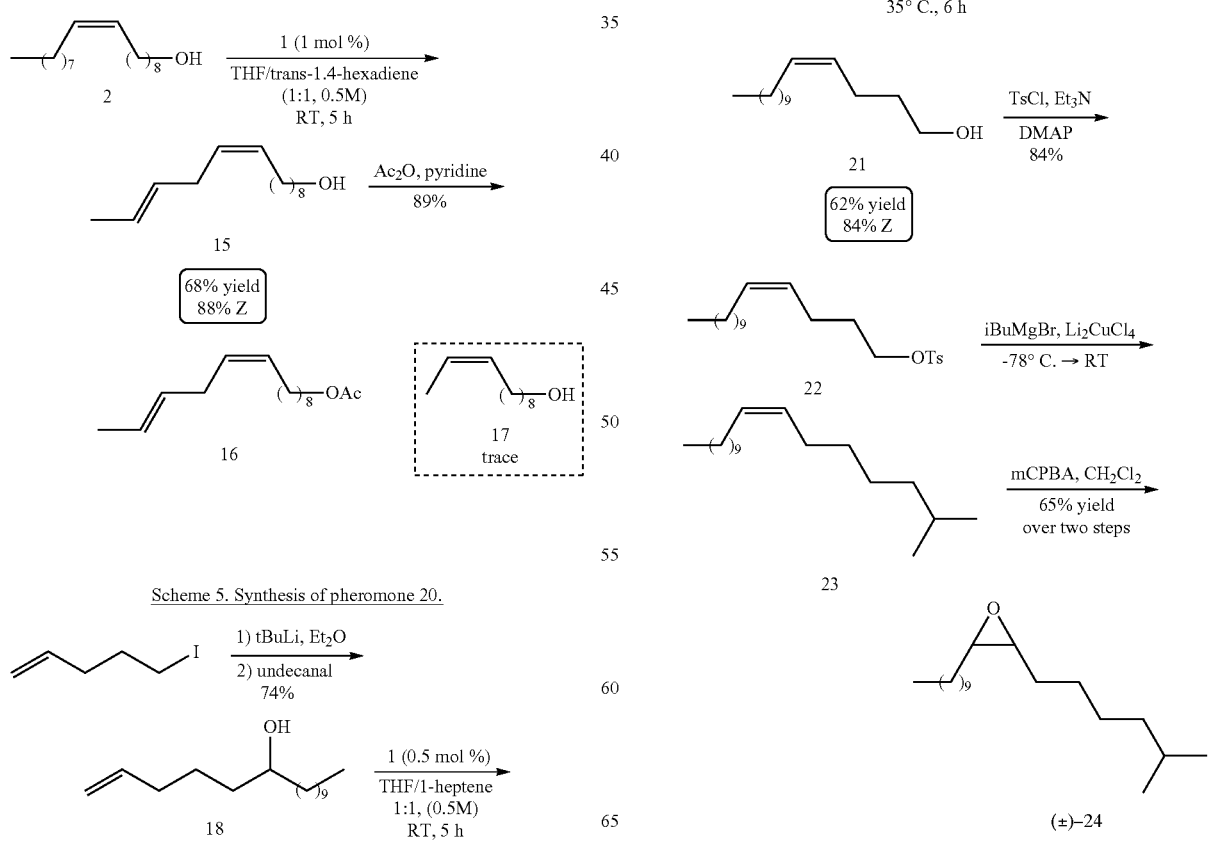

Example 1

(Z)-Tetradec-9-en-1-ol (3)

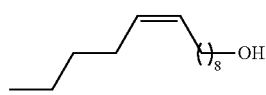

In a glovebox, a 20 mL vial was charged with oleyl alcohol (1.0 g, 3.7 mmol), 1-hexene (4 mL), and THF (4 mL). A solution of 1 (0.023 g, 1 mol %) in THF (0.5 mL) was added, and the mixture was stirred in an open vial for 5 hours. The vial was removed from the glovebox, the reaction was quenched with excess ethyl vinyl ether, and the solvent was removed in vacuo. Flash chromatography of the residue (SiO$_2$, using a gradient of hexanes to 20% EtOAc in hexanes) provided 3 (0.73 g, 77% yield, 86% Z as determined by $^1$H-NMR) as a colorless oil; $^1$H NMR (CDCl$_3$): δ 5.35 (2H, m), 3.64 (2H, td, J=6.6, 5.3 Hz), 2.02 (4H, m), 1.57 (2H, m), 1.22-1.39 (15H, m), 0.90 (3H, t, J=7.1 Hz); $^{13}$C NMR (CDCl$_3$): δ 129.9, 129.8, 63.1, 32.8, 32.0, 29.8, 29.5, 29.4, 29.2, 27.2, 26.9, 25.7, 22.4, 14.0; HRMS (FAB): 213.2215, [C$_{14}$H$_{28}$O+H]$^+$ requires 213.2218.

Example 2

(Z)-Hexadec-11-en-1-ol (5)

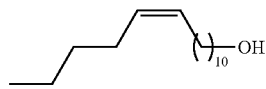

According to the procedure for compound 3, 11-eicosenol (1.3 g, 4.4 mmol) and 1-hexene (6 mL) in THF (6 mL) were reacted with 1 (0.028 g, 1 mol %) to provide 5 (0.84 g, 76% yield, 86% Z as determined by $^1$H-NMR) as a colorless oil; $^1$H NMR (CDCl$_3$): δ 5.36 (2H, m), 3.64 (2H, td, J=6.5, 5.3 Hz), 2.02 (4H, m), 1.56 (2H, m), 1.23-1.38 (19H, m), 0.90 (3H, t, J=7.2 Hz); $^{13}$C NMR (CDCl$_3$): δ 129.9 (2C), 63.1, 32.8, 32.0, 29.8, 29.6 (2C), 29.5, 29.4, 29.3, 27.2, 26.9, 25.8, 22.4, 14.0; HRMS (FAB): 241.2536, [C$_{16}$H$_{32}$O+H]$^+$ requires 241.2531.

Example 3

(Z)-Hexadec-11-enal (6)

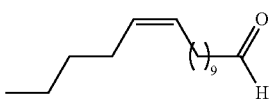

DMSO (0.11 mL, 1.6 mmol) was added dropwise to a solution of oxalyl chloride (0.080 mL, 0.96 mmol) in CH$_2$Cl$_2$ (5 mL) at −78° C., and after 5 minutes a solution of alcohol 5 (0.21 g, 0.87 mmol) in CH$_2$Cl$_2$ (0.9 mL) was added. After stirring for 15 minutes at the same temperature, triethylamine (0.61 mL, 4.4 mmol) was added. The mixture was warmed to room temperature, diluted with Et$_2$O, washed sequentially with 1M HCl, saturated aqueous NaHCO$_3$, brine, dried with Na$_2$SO$_4$, and the solvent was removed in vacuo. Flash chromatography of the residue (SiO$_2$, 10% EtOAc in hexanes) provided 6 (0.20 g, 95% yield, 86% Z as determined by $^1$H-NMR) as a colorless oil; $^1$H NMR (CDCl$_3$): δ 9.76 (1H, t, J=1.9 Hz), 5.36 (2H, m), 2.42 (2H, td, J=7.4, 1.9 Hz), 2.02 (4H, m), 1.63 (2H, m), 1.24-1.36 (16H, m), 0.90 (3H, t, J=7.2 Hz); $^{13}$C NMR (CDCl$_3$): δ 202.9, 129.9, 129.8, 43.9, 32.0, 29.8, 29.5, 29.4 (2C), 29.3, 29.2, 27.2, 26.9, 22.4, 22.1, 14.0; HRMS (FAB): 237.2209, [C$_{16}$H$_{30}$O−H]$^+$ requires 237.2218.

Example 4

(Z)-Dodec-9-en-1-ol (7)

In a glovebox, a 25 mL Schlenk flask was charged with oleyl alcohol (1.0 g, 3.7 mmol) and THF (2.5 mL). A solution of 1 (0.047 g, 2 mol %) in THF (0.5 mL) was added and the container was sealed and removed from the glovebox. The flask was attached to a Schlenk line and after three pump/refill cycles, under a positive pressure of argon, the Teflon plug was removed and replaced with a rubber septum. A needle was introduced into the flask and placed into the reaction solution. A slow bubble of 1-butene was introduced and the reaction was allowed to stir with bubbling 1-butene for 4 hours. The reaction was quenched with excess ethyl vinyl ether, and the solvent was removed in vacuo. Flash chromatography of the residue (SiO$_2$, using a slow gradient of hexanes to 9% EtOAc in hexanes) provided 7 (0.27 g, 40% yield, 77% Z as determined by $^{13}$C-NMR) as a colorless oil; $^1$H NMR (CDCl$_3$): δ 5.29-5.45 (2H, m), 3.63 (2H, t, J=6.6 Hz), 1.94-2.06 (4H, m), 1.56 (2H, p, J=6.7 Hz), 1.29 (11H, m), 0.95 (3H, m); $^{13}$C NMR (CDCl$_3$): δ 131.6, 129.3, 63.1, 32.8, 32.6, 29.8, 29.5, 29.4, 29.2, 29.1, 20.5, 14.4; HRMS (FAB): 184.1830, [C$_{12}$H$_{24}$O]+ requires 184.1827.

Example 5

(Z)-Dodec-9-en-1-yl acetate (8)

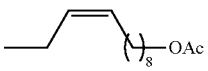

Acetic anhydride (0.17 mL, 1.8 mmol), then pyridine (90 μL, 1.1 mmol), were added sequentially to alcohol 7 (0.17 g, 0.93 mmol) in CH$_2$Cl$_2$ (1.8 mL), and stirred at room temperature for 17 hours. The mixture was diluted with diethyl ether, washed with saturated aqueous NaHCO$_3$, then brine, dried with Na$_2$SO$_4$, and concentrated. Flash chromatography of the residue (SiO$_2$, 5% EtOAc in hexanes) provided 8 (0.18 g, 87% yield, 74% Z as determined by $^{13}$C-NMR) as a colorless oil; $^1$H NMR (CDCl$_3$): δ 5.28-5.43 (2H, m), 4.05 (2H, t, J=6.8 Hz), 2.04 (7H, m), 1.61 (2H, td, J=9.8, 8.7, 4.6 Hz), 1.29 (10H, m), 0.95 (3H, m); $^{13}$C NMR (CDCl$_3$): δ 171.3, 131.6, 129.3, 64.7, 32.6, 29.8, 29.5, 29.3, 29.2, 28.7, 26.0, 21.1, 20.6, 14.5; HRMS (FAB): 227.2045, [$C_{14}H_{26}O_2$+H]+ requires 227.2006.

Example 5a (Z)-Hexadec-11-en-1-yl acetate (5-Ac)

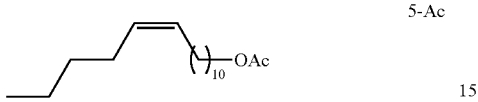

5-Ac

Applying acetylation reaction conditions analogous to those yielding 8 to (Z)-hexadec-11-en-1-ol (5) would reasonably be expected to yield the analogous (Z)-Hexadec-11-en-1-yl acetate (5-Ac).

Example 6

(Z)-Tetradec-11-en-1-ol (9)

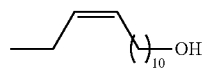

9

According to the procedure for compound 7, 11-eicosenol (1.1 g, 3.7 mmol) and THF (3 mL) were reacted with 1 (0.047 g, 2 mol %) and 1-butene to provide 9 (0.37 g, 47% yield, 76% Z as determined by $^{13}$C-NMR) as a colorless oil; $^1$H NMR (CDCl$_3$): δ 5.29-5.45 (2H, m), 3.63 (2H, t, J=6.6 Hz), 1.94-2.06 (4H, m), 1.56 (2H, dt, J=13.5, 6.7 Hz), 1.27, (15H, m), 0.96 (3H, m); $^{13}$C NMR (CDCl$_3$): δ 131.7, 129.5, 63.2, 33.0, 29.9, 29.7, 29.7, 29.7, 29.6, 29.4, 27.2, 25.9, 20.7, 14.6; HRMS (FAB): 212.2135, [$C_{14}H_{28}O$]+ requires 212.2140.

Example 7

(Z)-Tetradec-11-en-1-yl acetate (10)

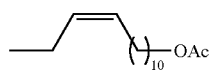

10

Acetic anhydride (0.17 mL, 1.8 mmol), then pyridine (86 μL, 1.1 mmol), were added sequentially to alcohol 7 (0.19 g, 0.89 mmol) in CH$_2$Cl$_2$ (1.8 mL), and stirred at room temperature for 12 hours. The mixture was diluted with diethyl ether, washed with saturated aqueous NaHCO$_3$, then brine, dried with Na$_2$SO$_4$, and concentrated. Flash chromatography of the residue (SiO$_2$, 5% EtOAc in hexanes) provided 10 (0.19 g, 84% yield, 77% Z as determined by $^{13}$C-NMR) as a colorless oil; $^1$H NMR (CDCl$_3$): δ 5.29-5.43 (2H, m), 4.05 (2H, t, J=6.8 Hz), 2.04 (7H, m), 1.61 (2H, m), 1.27 (14H, m), 0.95 (3H, m); $^{13}$C NMR (CDCl$_3$): δ 171.4, 131.7, 129.4, 64.8, 32.7, 29.9, 29.7 (2C), 29.4 (2C), 28.7, 27.2, 26.1, 21.2, 20.7, 14.6; HRMS (FAB): 255.2324, [$C_{16}H_{30}O_2$+H]$^+$ requires 255.2319.

Example 8

(Z)-Dodec-8-en-1-ol (12)

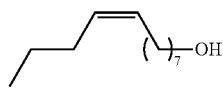

12

In a glovebox, a 20 mL vial was charged with 8-nonenol (0.58 g, 4.1 mmol), 1-pentene (4 mL), and THF (4 mL). A solution of 1 (0.026 g, 1 mol %) in THF (0.5 mL) was added, and the mixture was stirred in an open vial for 4 hours. The vial was removed from the glovebox, the reaction was quenched with excess ethyl vinyl ether, and the solvent was removed in vacuo. Flash chromatography of the residue (SiO$_2$, using a gradient of hexanes to 20% EtOAc in hexanes) provided 12 (0.56 g, 73% yield, 86% Z as determined by $^1$H-NMR) as a colorless oil; $^1$H NMR (CDCl$_3$): δ 5.36 (2H, m), 3.64 (2H, br t, J=5.3 Hz), 2.01 (4H, m), 1.36 (2H, m), 1.28-1.40 (11H, m), 0.90 (3H, t, J=7.4 Hz); $^{13}$C NMR (CDCl$_3$): δ 130.0, 129.7, 63.1, 32.8, 29.3 (4C), 27.2, 25.7, 22.9, 13.8; HRMS (EI): 184.1805, [$C_{12}H_{24}O$]+ requires 184.1827.

Example 9

(Z)-Dodec-8-en-1-yl acetate (13)

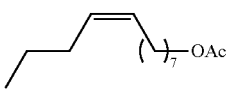

13

By cross metathesis of nonenyl acetate: according to the procedure for compound 12, 8-nonenyl acetate (0.76 g, 4.1 mmol) and 1-pentene (4 mL) in THF (4 mL) were reacted with 1 (0.026 g, 1 mol %) to provide 13 (0.60 g, 65% yield, 85% Z as determined by $^1$H-NMR) as a colorless oil; $^1$H NMR (CDCl$_3$): δ 5.36 (2H, m), 4.05 (2H, t, J=6.8 Hz), 2.05 (3H, s), 2.01 (4H, m), 1.62 (2H, m), 1.27-1.41 (10H, m), 0.90 (3H, t, J=7.4 Hz); $^{13}$C NMR (CDCl$_3$): δ 171.2, 129.9, 129.8, 64.7, 29.7, 29.3, 29.2 (2C), 28.6, 27.2, 25.9, 22.9, 21.0, 13.8; HRMS (EI): 227.2021, [C14H26O+H]+ requires 227.2011.

By acetylation of compound 2: According to the procedure for compound 6, Ac$_2$O (0.29 mL, 3.0 mmol), pyridine (0.14 mL, 1.8 mmol), and alcohol 12 (0.28 g, 1.5 mmol) were reacted to provide 13 (19 g, 90% yield, 86% Z as determined by $^1$H-NMR) as a colorless oil.

Example 10

(9Z,12E)-Tetradeca-9,12-dien-1-ol (15)

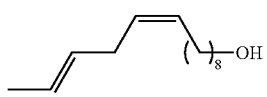

15

According to the procedure for compound 3, oleyl alcohol (1.0 g, 3.7 mmol) and 1,4-trans-hexadiene (4 mL) in THF (4 mL) were reacted with 1 (0.023 g, 1 mol %) to provide 15 0.53 g, 68% yield, 88% Z as determined by $^1$H-NMR) as a colorless oil; $^1$H NMR (CDCl$_3$): δ 5.32-5.49 (4H, m), 3.64 (2H, br t, J=6.6 Hz), 2.71 (2H, m), 2.03 (2H, m), 1.03 (3H, m), 1.56 (2H, m), 1.25-1.39 (11H, m); $^{13}$C NMR (CDCl$_3$): δ 130.4, 129.6, 127.7, 125.1, 63.1, 32.8, 30.4, 29.6, 29.5, 29.4, 29.2, 27.1, 25.7, 17.9; HRMS (FAB): 209.1906, [C$_{14}$H$_{26}$O−H]+ requires 209.1905.

Example 11

(9Z,12E)-Tetradeca-9,12-dien-1-yl acetate (16)

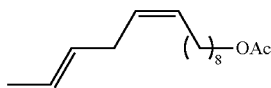

16

Acetic anhydride (3.1 mmol, 0.29 mL), then pyridine (1.8 mmol, 0.14 mL), were added sequentially to alcohol 15 (1.5 mmol, 0.32 g) in CH$_2$Cl$_2$ (3 mL), and stirred at room temperature for 18 hours. The mixture was diluted with diethyl ether, washed with saturated aqueous NaHCO$_3$, then brine, dried with Na$_2$SO$_4$, and concentrated. Flash chromatography of the residue (SiO$_2$, 10% EtOAc in hexanes) provided 16 (0.34 g, 89% yield, 88% Z as determined by $^1$H-NMR) as a colorless oil; $^1$H NMR (CDCl$_3$): δ 5.31-5.49 (4H, m), 4.05 (2H, t, J=6.8 Hz), 2.72 (2H, m), 2.05 (3H, s), 2.02 (2H, m), 1.65 (2H, m), 1.61 (2H, m), 1.24-1.38 (11H, m); $^{13}$C NMR (CDCl$_3$): δ 171.3, 130.4, 129.6, 127.7, 125.1, 64.7, 30.4, 29.6, 29.4, 29.2 (2C), 28.6, 27.1, 25.9, 21.0, 17.9; HRMS (FAB): 251.2000, [C$_{16}$H$_{28}$O$_2$−H]$^+$ requires 251.2011.

Example 12

(Z)-Hexadec-1-en-6-ol (18)

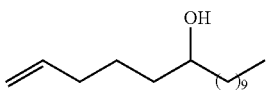

18

A solution of tert-butyllithium (19 mL, 1.7 M in pentanes) was added dropwise to a minus 78° C. solution of 5-iodopentene (3.0 g, 15 mmol) in Et$_2$O (25 mL), which was subsequently warmed to room temperature over 1 hour. The solution was re-cooled to −78° C., and undecanal (2.4 mL, 12 mmol) was added dropwise. The solution was let to warm to room temperature, washed with saturated NaHCO$_3$ (aq.), then brine, dried with Na$_2$SO$_4$, and the solvent was removed in vacuo. Flash chromatography of the residue (SiO$_2$, 10% EtOAc in hexanes) yielded 18 (4.2 g, 74%) as a colorless solid; $^1$H NMR (CDCl$_3$): δ 5.81 (1H, m), 5.01 (1H, m), 4.95 (1H, m), 3.60 (1H, m), 2.08 (2H, m), 1.37-1.58 (7H, m), 1.22-1.34 (16H, m), 0.88 (3H, t, J=6.9 Hz); $^{13}$C NMR (CDCl$_3$): δ 138.8, 114.6, 71.9, 37.5, 36.9, 33.8, 31.9, 29.7, 29.6 (3C), 29.35, 25.7, 24.9, 22.7, 14.1.

Example 13

(Z)-Henicos-6-en-11-ol (19)

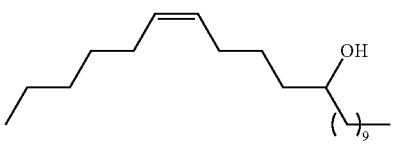

19

According to the procedure for compound 12, compound 18 (1.0 g, 4.2 mmol) and 1-heptene (4 mL) in THF (4 mL) were reacted with 1 (0.015 g, 0.5 mol %) to provide 19 (0.91 g, 70% yield, 88% Z as determined by quantitative $^{13}$C-NMR) as a colorless oil; $^1$H NMR (CDCl$_3$): δ 5.36 (2H, m), 3.59 (1H, m), 2.03 (4H, m), 1.21-1.54 (29H, m), 0.88 (6H, m); $^{13}$C NMR (CDCl$_3$): δ 130.4, 129.4, 71.9, 37.6, 37.1, 31.9, 31.6, 29.7 (2C), 29.6 (2C), 29.4 (2C), 27.2 (2C), 25.8, 25.7, 22.7, 22.6, 14.1 (2C); HRMS (FAB): 309.3162, [C$_{21}$H$_{42}$O−H]+ requires 309.3157.

Example 14

(Z)-Henicos-6-en-11-one (20)

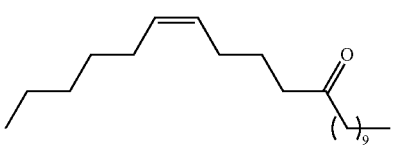

20

According to the procedure for compound 6, DMSO (0.080 mL, 1.1 mmol), oxalyl chloride (0.060 mL, 0.67 mmol), alcohol 19 (0.19 g, 0.61 mmol), and Et$_3$N (0.42 mL, 3.1 mmol) were reacted to yield 20 (0.17 g, 91% yield, 88% Z as determined by quantitative $^{13}$C-NMR) as a colorless oil; $^1$H NMR (CDCl$_3$): δ 5.39 (1H, m), 5.31 (1H, m), 2.39 (2H, t, J=7.5 Hz), 2.38 (2H, t, J=7.6 Hz), 2.04 (2H, m), 1.99 (2H, m), 1.63 (2H, m), 1.56 (2H, m), 1.20-1.37 (20H, m), 0.88 (6H, m); $^{13}$C NMR (CDCl$_3$): δ 211.4, 131.0, 128.7, 42.9, 42.1, 31.9, 31.5, 29.6, 29.4 (2C), 29.3 (2C), 23.9, 22.7, 22.6, 14.1 (2C); HRMS (FAB): 309.3148, [C$_{21}$H$_{40}$O+H]$^+$ requires 309.3157.

Example 15

(Z)-Pentadec-4-en-1-ol (21)

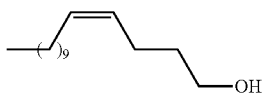

In a glovebox, a 20 mL vial was charged with 4-pentenol (410 μL, 3.98 mmol), 1-dodecene (4.4 mL), and THF (2.7 mL). A solution of 1 (0.025 g, 1 mol %) in THF (0.5 mL) was added, and the mixture was stirred in an open vial for 6 hours at 35° C. The vial was removed from the glovebox, the reaction was quenched with excess ethyl vinyl ether, and the solvent was removed in vacuo. Flash chromatography of the residue (SiO$_2$, using a gradient of hexanes to 8% EtOAc in hexanes) provided 21 (0.56 g, 62% yield, 84% Z as determined by $^{13}$C-NMR) as a colorless oil; $^1$H NMR (CDCl$_3$): δ 5.38 (2H, m), 3.65 (2H, m), 1.95-2.14 (4H, m), 1.63 (2H, m), 1.52 (1H, s), 1.25 (16H, m), 0.87 (3H, t, J=6.9 Hz); $^{13}$C NMR (100 Hz, CDCl$_3$): δ 131.0, 128.9, 62.8, 32.8, 32.1, 29.9, 29.8, 29.7 (2C), 29.5 (2C), 29.3, 23.7, 22.8, 14.2; HRMS (FAB): 227.2372, [C$_{15}$H$_{30}$O+H]$^+$ requires 227.2369.

Example 16

(Z)-Pentadecen-4-en-1-yl 4-methylbenzenesulfonate (22)

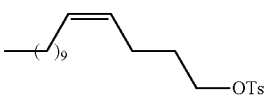

A 10 mL round bottom flask was charged with 21 (0.48 g, 2.12 mmol), Et3N (590 μL, 4.24 mmol), 4-dimethylaminopyridine (0.03 g, 0.21 mmol), and CH$_2$Cl$_2$ (5 mL) under an argon atmosphere. The solution was cooled to 0° C., and a solution of 4-toluenesulfonyl chloride (0.61 g, 3.18 mmol) in CH$_2$Cl$_2$ (1 mL) was added drop wise. The mixture was stirred vigourously for 4 hours at room temperature. The reaction mixture was treated with saturated aqueous NaHCO$_3$ (10 mL). After stirring at room temperature for 20 minutes, ethyl acetate (20 mL) was added. The organic layer was separated and washed with water (3×100 mL) and brine (50 mL), and dried over MgSO4. The solution was filtered and the solvent was removed in vacuo. Flash chromatography of the residue (SiO$_2$, using a gradient of 2:1 hexanes/CH$_2$Cl$_2$ to 1:1 hexanes/CH$_2$Cl$_2$) provided 22 (0.68 g, 84% yield, 84% Z as determined by $^{13}$C-NMR) as a colorless oil; $^1$H NMR (CDCl$_3$): δ 7.79 (2H, d, J=8.3 Hz), 7.33 (2H, d, J=8.9 Hz), 5.19-5.40 (2H, m), 4.02 2H, t, J=6.4 Hz), 2.44 (3H, s), 1.91-2.08 (4H, m), 1.66-1.71 (2H, m), 1.25 (16H, m), 0.88 (3H, t, J=7.0 Hz); $^{13}$C NMR (100 Hz, CDCl$_3$): δ 144.8, 144.7, 133.3, 131.8, 129.9, 128.0, 127.8, 127.4, 70.2, 32.6, 32.0, 29.7 (2C), 29.6 (2C), 29.5, 29.4, 29.0, 27.3, 23.1, 22.8, 14.3; HRMS (FAB): 381.2477, [C$_{22}$H$_{36}$O$_3$S+H]+ requires 381.2458.

Example 17 cis-7,8-Epoxy-2-methyloctadecane ((±)-24)

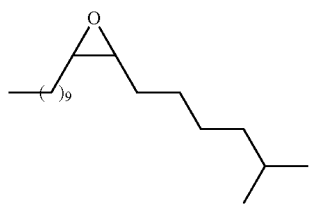

A 10 mL vial was charged with 22 (0.62 g, 1.63 mmol) and THF (2.2 mL) under an argon atmosphere and cooled to −78° C. 2 M isobutylmagnesium bromide in Et$_2$O (1.2 mL, 2.45 mmol) was added. Next, 0.1M Li$_2$CuCl$_4$ in THF (160 μL, 0.016 mmol) was added in one portion, and the reaction mixture was warmed to room temperature and allowed to stir overnight. An ice-cooled saturated aqueous NH4Cl solution (5 mL) was added and the solution was extracted with pentane (3×5 mL). The pentane extract was washed with water (10 mL) and brine (10 mL), dried over MgSO4, and concentrated in vacuo. Flash chromatography of the reside (SiO$_2$, using hexanes) provided a colorless oil that was used in the next step without further purification.

The crude product was taken up in CH$_2$Cl$_2$ (12 mL) and cooled to 0° C. A solution of mCBPA (0.35 g, 2 mmol) in CH$_2$Cl$_2$ (12 mL) was added slowly. The reaction was warmed to room temperature and stirred for 3.5 hours. A saturated aqueous NaHCO3 solution (25 mL) was added and the organic layer was dried over MgSO$_4$, filtered, and concentrated in vacuo. Flash chromatography of the residue (SiO$_2$, using a gradient of 1% EtOAc in hexanes to 15% EtOAc in hexanes) provided (±)-24 (0.30 g, 65% yield, 83% cis-isomer as determined by $^1$H NMR). $^1$H NMR (CDCl$_3$): δ 2.90 (2H, p, J=4.2 Hz), 1.49 (9H, m), 1.26 (16H, m), 1.14-1.2 (2H, m), 0.87 (9H, m); $^{13}$C NMR (CDCl$_3$): δ 57.4, 57.4, 39.1, 32.2, 32.1, 29.8, 29.7, 29.6, 29.5, 28.0 (3C), 27.5, 27.4, 26.8, 26.5, 26.2, 22.8 (2C), 14.3. HRMS (FAB): 282.2922, [C$_{19}$H$_{38}$]+ requires 282.2923.

Example 18

(Z)-tridec-8-en-1-yl acetate

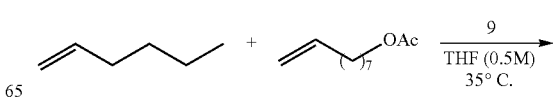

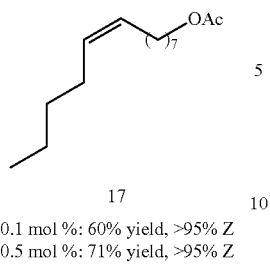

17
0.1 mol %: 60% yield, >95% Z
0.5 mol %: 71% yield, >95% Z

Reactions between 1-hexene and 8-nonenyl acetate were conducted using methods analogous to those described above using to form the pheromone derivative 17. When catalyzed by Ruthenium complex 1, the reaction proceeded in good yield (67%) with high Z-selectivity (91%) at a low catalyst loading (0.5 mol %).

When catalyzed by Ruthenium complex 9, under nominally identical conditions, the reaction proceeded to product with no observable formation of the E-isomer and in slightly higher yield (71%) at the same catalyst loading. Even at lower catalyst loading (to 0.1 mol %), the system still provided good yields of 17 (60%) while maintaining >95% Z-selectivity.

It is to be understood that while the invention has been described in conjunction with the preferred specific embodiments thereof, that the foregoing description and the examples that follow are intended to illustrate and not limit the scope of the invention. It will be understood by those skilled in the art that various changes may be made and equivalents may be substituted without departing from the scope of the invention, and further that other aspects, advantages and modifications will be apparent to those skilled in the art to which the invention pertains. In addition to the embodiments described herein, the present invention contemplates and claims those inventions resulting from the combination of features of the invention cited herein and those of the cited prior art references which complement the features of the present invention. Similarly, it will be appreciated that any described material, feature, or article may be used in combination with any other material, feature, or article, and such combinations are considered within the scope of this invention.

The disclosures of each patent, patent application, and publication cited or described in this document are hereby incorporated herein by reference, each in its entirety, for all purposes.

What is claimed:

1. A method of synthesizing a lepidopteran insect pheromone containing a Z-olefin metathesis product, said method comprising:
   (a) cross-metathesizing (i) a terminal olefin and an internal olefin or (ii) two terminal olefins in the presence of a hindered ruthenium metathesis catalyst to form the insect pheromone containing Z-olefin metathesis product and a side product;
   the hindered metathesis catalyst comprising a C—H activated olefin metathesis catalyst compound having a structure of Formula I:

(I)

wherein
   $X^1$ is a t-butyl carboxylate or a nitrate;
   $L^1$ is a carbene ligand having the structure of Formula (II):

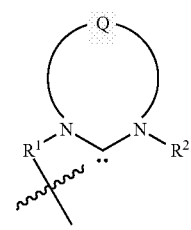

(II)

wherein,
   Q is ethylene (—CH$_2$—CH$_2$—);
   $R^1$ is an adamantylene group, where $R^1$ links $L^1$ and M and, together with $L^1$ and M, form one or more cyclic groups, and wherein M, $L^1$ and $R^1$ form an M-$R^1$-$L^1$ chelating ligand ring structure having a ring size of 5 atoms;
   $R^2$ is 2,4,6-trimethyl phenyl (mesityl), 2,6-methylisopropylphenyl (MIPP), or 2,6-diisopropylphenyl (DIPP);
   Y is O;
   $R^3$, $R^4$, $R^5$, and $R^6$ are each hydrogen;
   n is 1; and
   Z is alkyl.

2. The method of claim 1, wherein $R^2$ is 2,4,6-trimethyl phenyl (mesityl) or 2,6-di-isopropylphenyl (DIPP); $X^1$ is nitrate or pivalate; and $(Z)_n$ is isopropyl.

3. The method of claim 1, the C—H activated olefin metathesis catalyst compound comprising at least one of the following:

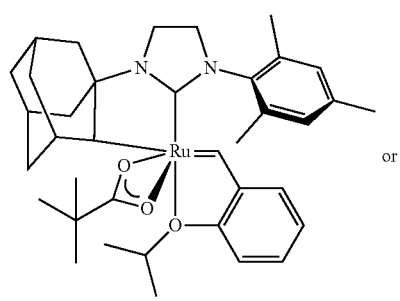

or

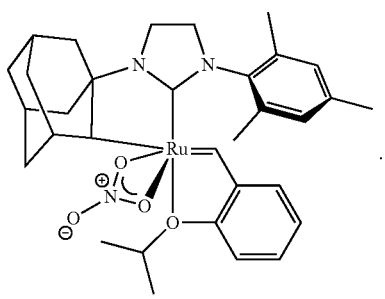

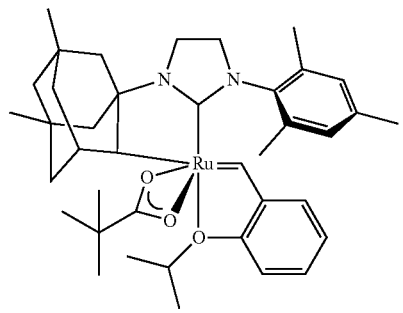
, or

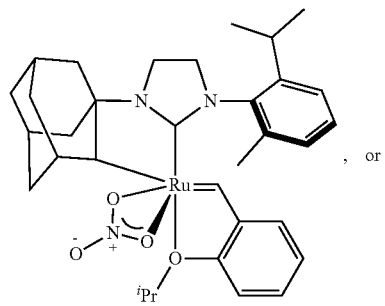
, or

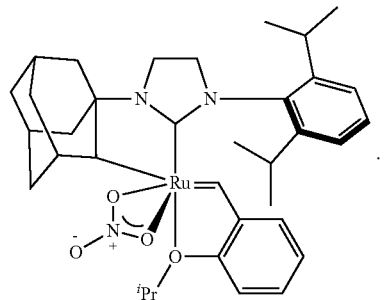

4. The method of claim 1, wherein the C—H activated olefin metathesis catalyst compound comprises:

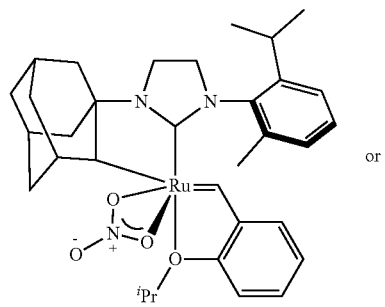
or

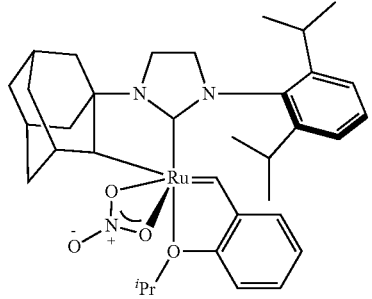

5. The method of claim 1, further comprising (b) applying conditions sufficient to remove the side product from the metathesis product the conditions comprising (a) providing sufficiently high temperature or sufficiently low pressure, or both, so as to preferentially volatilize the side product from the metathesis product or vice versa; (b) extracting the side product from the metathesis product with a solvent or (c) chromatographic methods.

6. The method of claim 1, the method comprising cross-metathesizing a terminal olefin and an internal olefin.

7. The method of claim 1, the method comprising cross-metathesizing two terminal olefins.

8. The method of claim 5, the method comprising applying the conditions sufficient to remove the side product from the metathesis product during the cross-metathesis reaction.

9. The method of claim 1, wherein at least one of the starting olefins comprises an alkenyl ester which contains 2 to 22 carbons; alkenyl halide which contains 2 to 22 carbons; alpha, omega-alkenyl diester which contains 4 to 40 carbons; alpha, omega-alkenyl dihalide which contains 4 to 40 carbons; alkene which contains 2 to 44 carbons; alkenol which contains 2 to 22 carbons; alkene diol of which contains 4 to 40 carbons; or a derivative thereof.

10. The method of claim 1, wherein the terminal olefin has a —CH=CH$_2$ motif and the internal olefin has a —CH=CH— motif.

11. The method of claim 1, wherein at least one of the starting olefins comprises a terminal or internal olefin optionally comprising at least one aldehyde, amino, amide, hydroxyl or protected hydroxyl, branched alkyl, alkylaryl, alkylheteroaryl, $C_{1-6}$ alkenyl, $C_{1-6}$ alkynyl, $C_{1-6}$ alkoxy, azide, —N—C(O)—$C_{1-6}$ alkyl, —O—C(O)—$C_{1-6}$ alkyl, —N—C(O)—O—$C_{1-6}$ alkyl, —O—C(O)—O—$C_{1-6}$ alkyl, aryl, carboxylic acid, carboxy ester, cyano, epoxide, fluorinated or perfluorinated alkyl, halo (fluorine, chloro, bromo, iodo), heterocyclyl, heteroaryl, or ketone.

12. The method of claim 1, wherein at least one of the starting olefins comprises allyl acetate, 2-(allyloxy)ethanol, 1-propene, 1-butene, 1-pentene, 1-hexene, 3-hexene, trans-1,4-hexadiene, 1-heptene, 1-octene, 1-nonene, 5-decene, 2-buten-1-ol, 2-butenylacetate, 2-butenylbromide, 2-butenylchloride, 2-butenyliodide, 4-pentenol, 4-pentenyl acetate, 4-pentenyl bromide, 4-pentenyl chloride, 4-pentenyl iodide, 5-hexen-1-ol, 5-hexenyl acetate, 5-hexenyl bromide, 5-hexenyl chloride, 5-hexenyl iodide, 3-hexenol, 3-hexenyl acetate, 1-bromo-3-hexene, 1-chloro-3-hexene, 8-nonen-1-ol, 8-nonen-1-yl acetate, 8-nonen-1-yl bromide, 8-nonen-1-yl chloride, 8-nonen-1-yl iodide, 1-dodecene, oleyl alcohol (cis-9-octadecen-1-ol), oleyl acetate (cis-9-octadecen-1-yl acetate), oleyl bromide (cis-9-octadecen-1-yl bromide), oleyl chloride (cis-9-octadecen-1-yl chloride), oleyl iodide (cis-9-octadecen-1-yl iodide), elaidyl alcohol (9E-octadecen-1-ol), elaidyl acetate (9E-octadecen-1-yl acetate), 11-docosene, 10-methyl undecenoate, 11-eicosenol, methyl 5-eicosenoate, 5-eicosneyl acetate, methyl 11-eicosenoate, 11-eicosenyl acetate, palmitoleyl alcohol (cis-9-hexadecen-1-ol), erucyl alcohol (cis-13-docosen-1-ol), erucyl acetate, erucyl bromide, or erucyl chloride.

13. The method of claim 1, wherein the side product comprises a $C_2$-$C_{10}$ olefin.

14. The method of claim 1, wherein the metathesis product comprises a compound having the formula: 3, 5, 5-Ac, 6-10, 12-13, 15-17, 19-22, or 24:

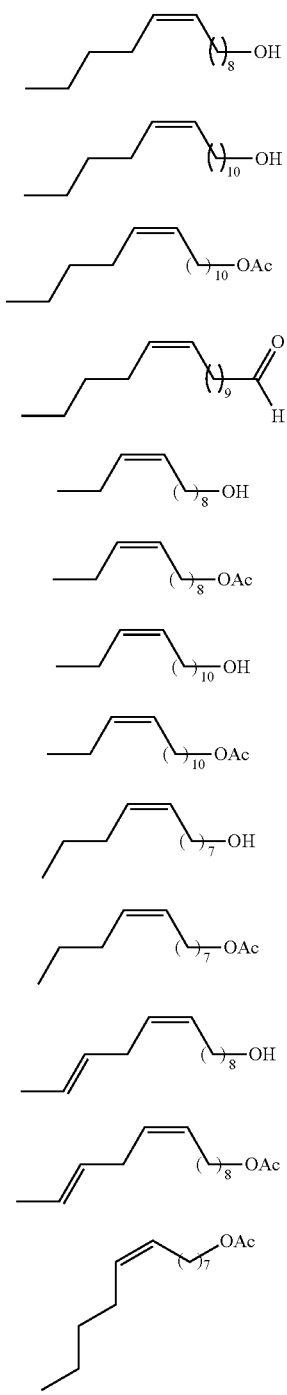

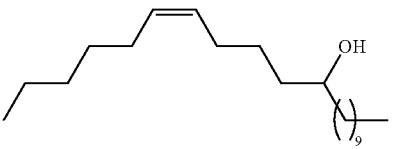

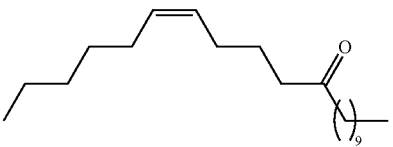

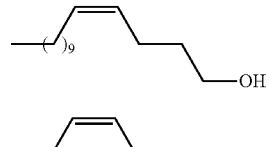

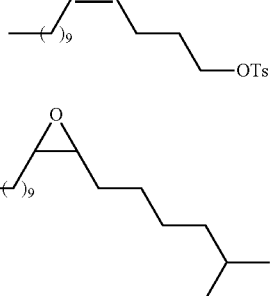

15. The method of claim 5, wherein the metathesis product is further purified by distillation or chromatography.

16. The method of claim 1, wherein the cross-metathesis reaction is conducted at at least one temperature in a range of from about 18° C. to about 200° C.

17. The method of claim 1, wherein the cis:trans isomeric ratio of the Z-olefin metathesis product is greater than 90:10.

18. The method of claim 5, the low pressure being less than about 50 mm Hg.

19. The method of claim 1, with the proviso that the reaction does not comprise the cross-metathesis of 1-hexene and 8-nonenyl acetate to form (Z)-tridec-8-en-1-yl acetate (17).

20. The method of claim 1, said method comprising:
(a) cross-metathesizing oleyl alcohol and 1-hexene in the presence of the hindered ruthenium metathesis catalyst to form (Z)-tetradec-9-en-1-ol (3) and 1-decene; or
(b) cross-metathesizing 11-eicosenol and and 1-hexene in the presence of the hindered ruthenium metathesis catalyst to form (Z)-hexadec-11-en-1-ol (5) and 1-decene; and optionally further comprising (1) optionally separating the (Z)-hexadec-11-en-1-ol (5) from the 1-decene, and acetylating the the (Z)-hexadec-11-en-1-ol (5) to form (Z)-hexadec-11-en-1-yl acetate (5-Ac); or (2) optionally separating the (Z)-hexadec-11-en-1-ol (5) from the 1-decene, and oxidizing the (Z)-hexadec-11-en-1-ol (5) to form (Z)-hexadec-11-enal (6); or
(c) cross-metathesizing oleyl alcohol and and 1-butene in the presence of the hindered ruthenium metathesis catalyst to form (Z)-dodec-9-en-1-ol (7) and 1-decene; and optionally further comprising optionally separating the (Z)-dodec-9-en-1-ol (7) from the 1-decene, and acetylating the (Z)-dodec-9-en-1-ol (7) to form (Z)-dodec-9-en-1-yl acetate (8); or
(d) cross-metathesizing 11-eicosenol and and 1-butene in the presence of the hindered ruthenium metathesis catalyst to form (Z)-tetradec-11-en-1-ol (9) and 1-decene; and optionally further comprising optionally separating the (Z)-tetradec-11-en-1-ol (9) and 1-decene, and acetylating the (Z)-tetradec-11-en-1-ol (9) to form (Z)-tetradec-11-en-1-yl acetate (10); or (e) cross-metathesizing 8-nonenol and 1-pentene in the presence of the hindered ruthenium metathesis catalyst to form (Z)-dodec-8-en-1-ol (12) and ethylene; and optionally further comprising optionally separating the (Z)-dodec-8-en-1-ol (12) and ethylene, and acetylating the (Z)-dodec-8-en-1-ol (12) to form (Z)-dodec-8-en-1-yl acetate (13); or (f) cross-metathesizing 8-nonenyl acetate and 1-pentene in the presence of the hindered ruthenium metathesis catalyst to form (Z)-dodec-8-en-1-yl acetate (13) and ethylene; or (g) cross-metathesizing oleyl alcohol and 1,4-trans-hexadiene in the presence of a hindered ruthenium metathesis catalyst to form (9Z,12E)-tetradeca-9,12-dien-ol (15) and 1-decene; and optionally further comprising optionally separating the (9Z,12E)-tetradeca-9,12-dien-ol (15) and 1-decene, and acetylating the (9Z,12E)-tetradeca-9,12-dien-ol (15) to form (9Z,12E)-tetradeca-9,12-dien-yl acetate (16); or (h) cross-metathesizing (Z)-hexadec-1-6-ol and 1-heptene to form (Z)-henicos-6-en-11-ol (19) and ethylene; and optionally further comprising optionally separating the (Z)-henicos-6-en-11-ol (19) and ethylene, and oxidizing the (Z)-henicos-6-en-11-ol (19) to form (Z)-henicos-6-en-11-one (20); or (i) cross-metathesizing 4-pentanol and 1-dodecene in the presence of a hindered ruthenium metathesis catalyst to form (Z)-pentadec-4-en-1-ol (21) and ethylene.

21. The method of claim 20, the hindered ruthenium metathesis catalyst comprising a compound having a structure:

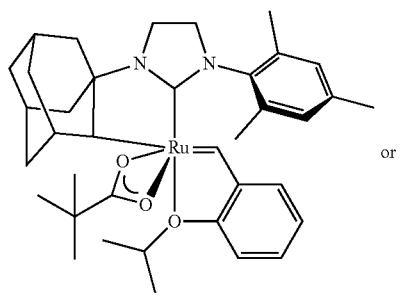

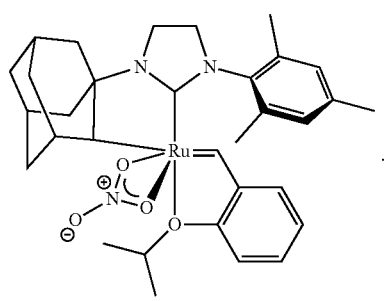

22. The method of claim 4, wherein the C—H activated olefin metathesis catalyst compound comprises:

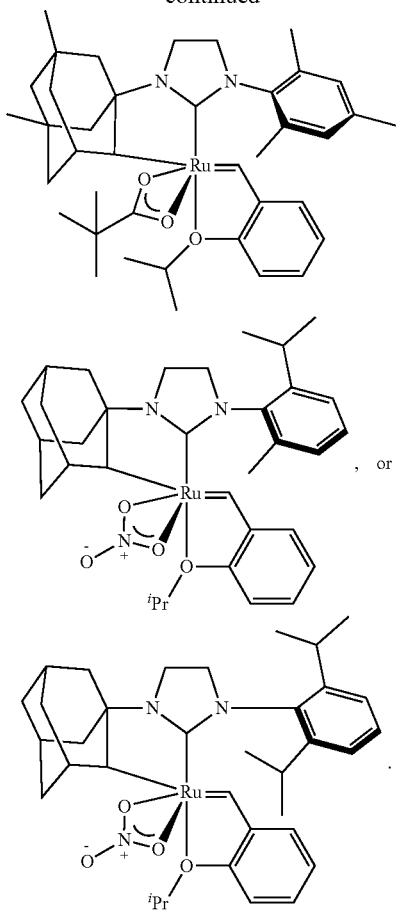

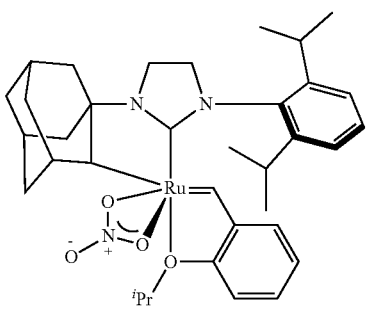

23. The method of claim 3, further comprising (b) applying conditions sufficient to remove the side product from the metathesis product, these conditions comprising (i) providing sufficiently high temperature or sufficiently low pressure, or both, so as to preferentially volatilize the side product from the metathesis product, or vice versa; (ii) extracting the side product from the metathesis product with a solvent; or (iii) chromatographic methods.

24. The method of claim 22, further comprising (b) applying conditions sufficient to remove the side product from the metathesis product, these conditions comprising (i) providing sufficiently high temperature or sufficiently low pressure, or both, so as to preferentially volatilize the side product from the metathesis product, or vice versa; (ii) extracting the side product from the metathesis product with a solvent; or (iii) chromatographic methods.

25. The method of claim 3, wherein at least one of the starting olefins comprises allyl acetate, 2-(allyloxy)ethanol, 1-propene, 1-butene, 1-pentene, 1-hexene, 3-hexene, trans-1,4-hexadiene, 1-heptene, 1-octene, 1-nonene, 5-decene, 2-buten-1-ol, 2-butenylacetate, 2-butenylbromide, 2-butenylchloride, 2-butenyliodide, 4-pentenol, 4-pentenyl acetate, 4-pentenyl bromide, 4-pentenyl chloride, 4-pentenyl iodide, 5-hexen-1-ol, 5-hexenyl acetate, 5-hexenyl bromide, 5-hexenyl chloride, 5-hexenyl iodide, 3-hexenol, 3-hexenyl acetate, 1-bromo-3-hexene, 1-chloro-3-hexene, 8-nonen-1-ol, 8-nonen-1-yl acetate, 8-nonen-1-yl bromide, 8-nonen-1-yl chloride, 8-nonen-1-yl iodide, 1-dodecene, oleyl alcohol (cis-9-octadecen-1-ol), oleyl acetate (cis-9-octadecen-1-yl acetate), oleyl bromide (cis-9-octadecen-1-yl bromide), oleyl chloride (cis-9-octadecen-1-yl chloride), oleyl iodide (cis-9-octadecen-1-yl iodide), elaidyl alcohol (9E-octadecen-1-ol), elaidyl acetate (9E-octadecen-1-yl acetate), 11-docosene, 10-methyl undecenoate, 11-eicosenol, methyl 5-eicosenoate, 5-eicosneyl acetate, methyl 11-eicosenoate, 11-eicosenyl acetate, palmitoleyl alcohol (cis-9-hexadecen-1-ol), erucyl alcohol (cis-13-docosen-1-ol), erucyl acetate, erucyl bromide, or erucyl chloride.

26. The method of claim 22, wherein at least one of the starting olefins comprises allyl acetate, 2-(allyloxy)ethanol, 1-propene, 1-butene, 1-pentene, 1-hexene, 3-hexene, trans-1,4-hexadiene, 1-heptene, 1-octene, 1-nonene, 5-decene, 2-buten-1-ol, 2-butenylacetate, 2-butenylbromide, 2-butenylchloride, 2-butenyliodide, 4-pentenol, 4-pentenyl acetate, 4-pentenyl bromide, 4-pentenyl chloride, 4-pentenyl iodide, 5-hexen-1-ol, 5-hexenyl acetate, 5-hexenyl bromide, 5-hexenyl chloride, 5-hexenyl iodide, 3-hexenol, 3-hexenyl acetate, 1-bromo-3-hexene, 1-chloro-3-hexene, 8-nonen-1-ol, 8-nonen-1-yl acetate, 8-nonen-1-yl bromide, 8-nonen-1-yl chloride, 8-nonen-1-yl iodide, 1-dodecene, oleyl alcohol (cis-9-octadecen-1-ol), oleyl acetate (cis-9-octadecen-1-yl acetate), oleyl bromide (cis-9-octadecen-1-yl bromide), oleyl chloride (cis-9-octadecen-1-yl chloride), oleyl iodide (cis-9-octadecen-1-yl iodide), elaidyl alcohol (9E-octadecen-1-ol), elaidyl acetate (9E-octadecen-1-yl acetate), 11-docosene, 10-methyl undecenoate, 11-eicosenol, methyl 5-eicosenoate, 5-eicosneyl acetate, methyl 11-eicosenoate, 11-eicosenyl acetate, palmitoleyl alcohol (cis-9-hexadecen-1-ol), erucyl alcohol (cis-13-docosen-1-ol), erucyl acetate, erucyl bromide, or erucyl chloride.

27. The method of claim 3, wherein the metathesis product comprises a compound having the formula: 3, 5, 5-Ac, 6-10, 12-13, 15-17, 19-22, or 24:

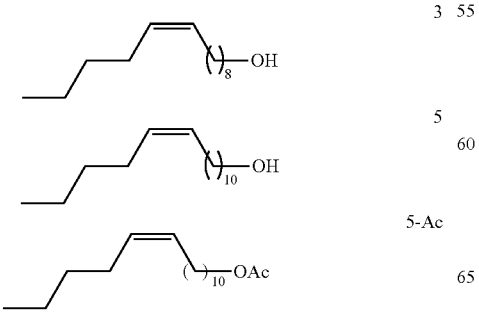

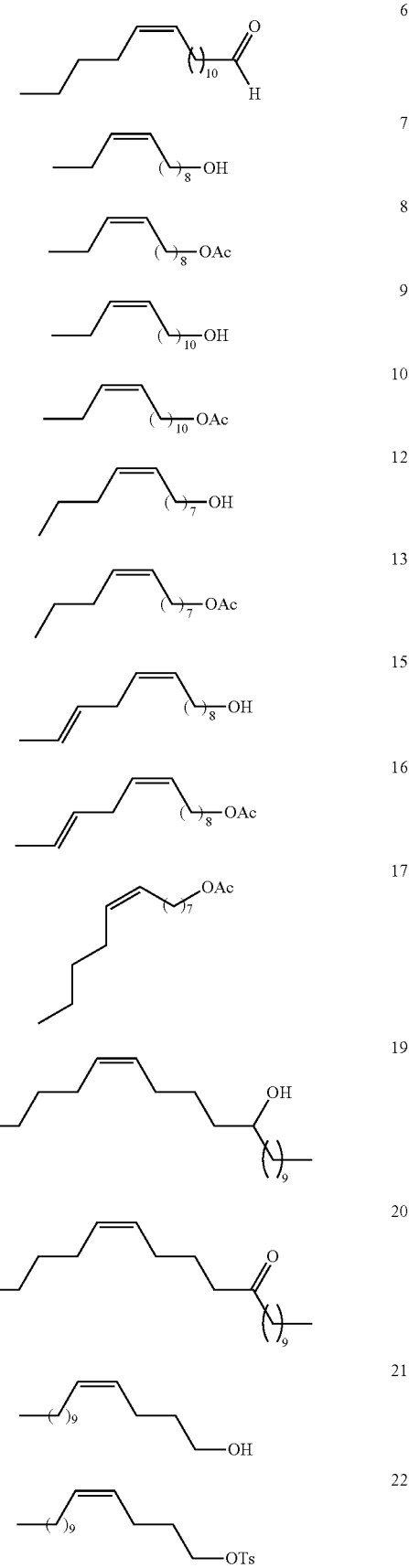

-continued
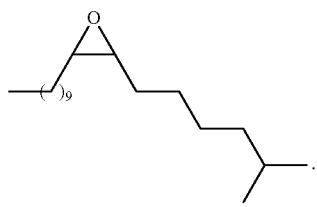
(±)-24
28. The method of claim 22, wherein the metathesis product comprises a compound having the formula: 3, 5, 5-Ac, 6-10, 12-13, 15-17, 19-22, or 24:
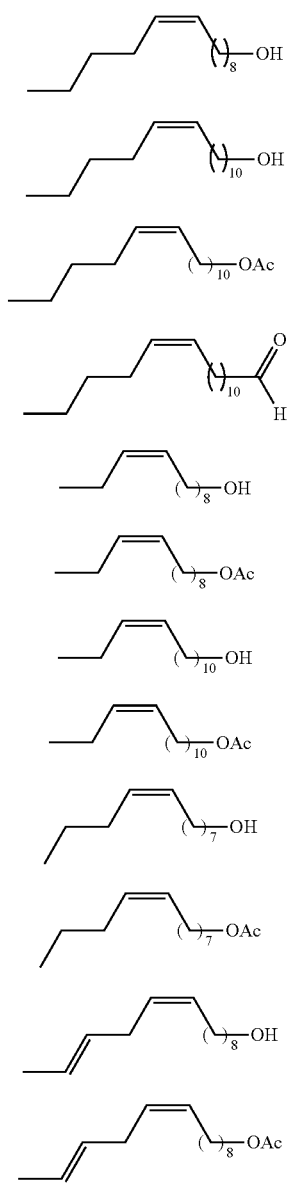
-continued
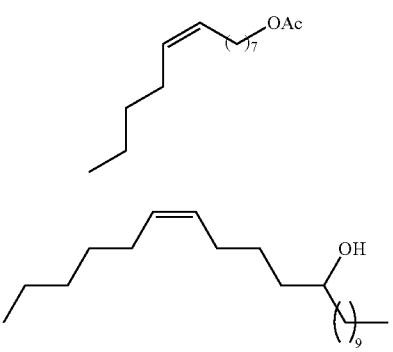
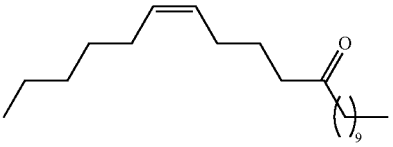
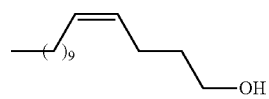
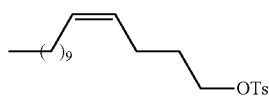
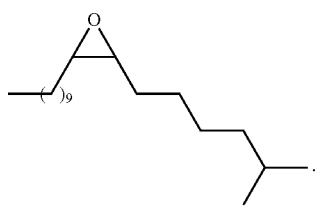
(±)-24
29. The method of claim 22, wherein the cis:trans isomeric ratio of the Z-olefin metathesis product is greater than 95:5.
30. The method of claim 20, the hindered ruthenium metathesis catalyst comprising a compound having a structure:
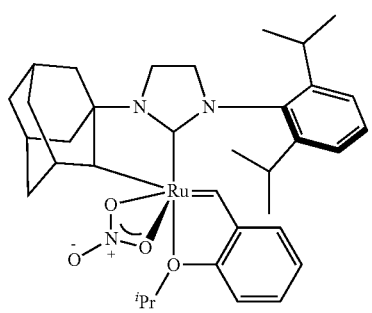
* * * * *